United States Patent
Chandrasekaran

(10) Patent No.: US 9,358,714 B2
(45) Date of Patent: Jun. 7, 2016

(54) STRUCTURED FILM CONTAINING BETA-NUCLEATING AGENT AND METHOD OF MAKING THE SAME

(75) Inventor: Neelakandan Chandrasekaran, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 643 days.

(21) Appl. No.: 13/324,130

(22) Filed: Dec. 13, 2011

(65) Prior Publication Data

US 2013/0149488 A1 Jun. 13, 2013

(51) Int. Cl.
*B32B 3/30* (2006.01)
*B29C 47/00* (2006.01)
(Continued)

(52) U.S. Cl.
CPC ........... *B29C 47/0057* (2013.01); *B29C 43/222* (2013.01); *B29C 47/065* (2013.01); *B29C 47/884* (2013.01); *B29C 55/06* (2013.01); *B29C 55/12* (2013.01); *B32B 3/30* (2013.01); *B32B 27/08* (2013.01); *B32B 27/12* (2013.01); *B32B 27/18* (2013.01); *B32B 27/32* (2013.01); *C08J 5/18* (2013.01); *B29C 47/0021* (2013.01); *B29C 55/04* (2013.01); *B29K 2105/0005* (2013.01); *B29K 2105/04* (2013.01); *B32B 2274/00* (2013.01); *B32B 2307/4026* (2013.01); *B32B 2307/41* (2013.01); *B32B 2307/42* (2013.01); *B32B 2307/516* (2013.01); *B32B 2307/54* (2013.01); *B32B 2307/546* (2013.01); *B32B 2307/558* (2013.01); *B32B 2307/704* (2013.01); *B32B 2307/706* (2013.01);

(Continued)

(58) Field of Classification Search
CPC .. B32B 3/30; Y10T 428/24008; B29C 43/222
USPC ...................................... 428/99, 98
See application file for complete search history.

(56) References Cited

U.S. PATENT DOCUMENTS

| 4,435,141 A | 3/1984 | Weisner |
| 4,775,310 A | 10/1988 | Fischer |

(Continued)

FOREIGN PATENT DOCUMENTS

| EP | 1816158 | 8/2007 |
| GB | 2323325 | 9/1998 |

(Continued)

OTHER PUBLICATIONS

International Search Report for International Application No. PCT/US2012/069152, dated Mar. 11, 2013.

(Continued)

*Primary Examiner* — Brent O'Hern

(57) ABSTRACT

A structured film of a semi-crystalline polyolefin and a beta-nucleating agent is disclosed. The structured film has a backing and upstanding posts attached to the backing. At least a portion of the film typically includes beta-spherulites. In some embodiments, the backing is microporous while the upstanding posts have lower porosity. A method of making a structured film is also disclosed. The method includes extruding a melt of a polyolefin and a beta-nucleating agent in the presence of a tool to provide the structured film having upstanding posts on a backing and cooling at least a portion of the structured film to a temperature sufficient to form beta-spherulites. In some embodiments, the method further includes stretching the structured film containing beta-spherulites to provide micropores in the backing.

20 Claims, 6 Drawing Sheets

(51) Int. Cl.
| | |
|---|---|
| *B29C 47/06* | (2006.01) |
| *B29C 47/88* | (2006.01) |
| *B32B 27/08* | (2006.01) |
| *B32B 27/12* | (2006.01) |
| *B32B 27/18* | (2006.01) |
| *B32B 27/32* | (2006.01) |
| *C08J 5/18* | (2006.01) |
| *B29C 43/22* | (2006.01) |
| *B29C 55/06* | (2006.01) |
| *B29C 55/12* | (2006.01) |
| *B29C 55/04* | (2006.01) |
| *B29K 105/00* | (2006.01) |
| *B29K 105/04* | (2006.01) |

(52) U.S. Cl.
CPC ...... *B32B 2307/718* (2013.01); *B32B 2555/02* (2013.01); *C08J 2323/14* (2013.01); *Y10T 428/24008* (2015.01); *Y10T 428/24504* (2015.01); *Y10T 428/24612* (2015.01)

(56) References Cited

U.S. PATENT DOCUMENTS

| | | | |
|---|---|---|---|
| 4,839,131 | A | 6/1989 | Cloeren |
| 4,894,060 | A | 1/1990 | Nestegard |
| 5,107,131 | A | 4/1992 | Okada et al. |
| 5,236,963 | A | 8/1993 | Jacoby et al. |
| 5,359,525 | A | 10/1994 | Weyenberg |
| 5,429,856 | A | 7/1995 | Krueger |
| 5,845,375 | A | 12/1998 | Miller |
| 5,868,987 | A | 2/1999 | Kampfer |
| 6,100,987 | A | 8/2000 | Kawakubo |
| 6,106,922 | A | 8/2000 | Cejka |
| 6,110,588 | A | 8/2000 | Perez |
| 6,132,660 | A | 10/2000 | Kampfer |
| 6,190,594 | B1 | 2/2001 | Gorman |
| 6,368,097 | B1 | 4/2002 | Miller |
| 6,368,742 | B2 | 4/2002 | Fisher |
| 6,420,024 | B1 | 7/2002 | Perez |
| 6,582,642 | B1 | 6/2003 | Buzzell |
| 6,632,850 | B2 | 10/2003 | Hughes |
| 6,669,887 | B2 | 12/2003 | Hilston |
| 6,708,378 | B2 | 3/2004 | Parellada |
| 6,767,492 | B2 | 7/2004 | Norquist |
| 6,815,048 | B2 | 11/2004 | Davidson |
| 6,927,857 | B2 | 8/2005 | Koele et al. |
| 7,214,334 | B2 | 5/2007 | Jens |
| 7,423,088 | B2 | 9/2008 | Mader |
| 7,682,689 | B2 | 3/2010 | Sadamitsu et al. |
| 7,897,078 | B2 | 3/2011 | Petersen |
| 2003/0036577 | A1* | 2/2003 | Hughes et al. ................ 521/82 |
| 2003/0148091 | A1 | 8/2003 | Ikeda et al. |
| 2004/0261231 | A1* | 12/2004 | Seth et al. ....................... 24/452 |
| 2005/0122531 | A1 | 6/2005 | Koele |
| 2005/0215963 | A1 | 9/2005 | Autran et al. |
| 2005/0288510 | A1 | 12/2005 | Mader et al. |
| 2006/0177632 | A1 | 8/2006 | Jacoby |
| 2007/0020448 | A1 | 1/2007 | Hubbard |
| 2007/0082154 | A1 | 4/2007 | Ambroise |
| 2007/0089279 | A1 | 4/2007 | Seth et al. |
| 2008/0000581 | A1 | 1/2008 | Nison |
| 2008/0233373 | A1 | 9/2008 | Coburn |
| 2009/0059229 | A1 | 3/2009 | Fukue |
| 2009/0258212 | A1 | 10/2009 | Jacoby |
| 2010/0301510 | A1 | 12/2010 | Coburn |
| 2011/0147475 | A1 | 6/2011 | Biegler |
| 2011/0151171 | A1 | 6/2011 | Biegler |

FOREIGN PATENT DOCUMENTS

| | | | |
|---|---|---|---|
| GB | 2323327 | 9/1998 | |
| GB | 2323328 | 9/1998 | |
| WO | WO 93/21262 | 10/1993 | |
| WO | WO 03-025049 | 3/2003 | |
| WO | WO 2006/023442 | 3/2006 | |
| WO | WO 2006023442 A1 * | 3/2006 | ............... B32B 3/10 |
| WO | WO 2010-065602 | 6/2010 | |
| WO | WO 2011/045683 | 4/2011 | |
| WO | WO 2011-097436 | 8/2011 | |
| WO | WO 2011-139940 | 11/2011 | |

OTHER PUBLICATIONS

International Search Report for International Application No. PCT/US2012/069165, dated Apr. 17, 2013.

ASTM Designation: D-1922-09, "Standard Test Method for Propagation Tear Resistance of Plastic Film and Thin Sheeting by Pendulum Method[1]", 2009, pp. 1-7.

ASTM Designation: D-3759/D3759M-05, "Standard Test Method for Breaking Strength and Elongation of Pressure-Sensitive Tape[1]", 2005, pp. 1-7.

ASTM Designation: D-6125-97 (Reapproved 2002), "Standard Test Method for Bending Resistance of Paper and Paperboard (Gurley Type Tester)[1]", 1997, pp. 1-5.

ASTM Designation: E-284-09a, "Standard Terminology of Appearance[1]", 2009, pp. 1-23.

ASTM Designation: F-316-80, "Standard Test Method for Pore Size Characteristics of Membrane Filters for Use With Aerospace Fluids[1]", 1980, pp. 872-878.

Chu, "Microvoid formation process during the plastic deformation of β-form polypropylene", *Polymer*, Aug. 1994, vol. 35, No. 16, pp. 3442-3448.

Chu, "Crystal transformation and micropore formation during uniaxial drawing of β-form polypropylene film", *Polymer*, 1995, vol. 36, No. 13, pp. 2523-2530.

Dow C700-35N PolyPropylene Resin, Medium Impact Copolymer, Dow Plastics Product Information, Mar. 2003, 2 pages.

Jones, "Crystalline Forms of Isotactic Polyprolpylene", Die Makromolekulare Chemie, 1964, vol. 75, No. 1 pp. 134-158.

U.S. Appl. No. 13/323,980, filed Dec. 13, 2011, entitled Method of Detecting a Component of an Article and Method of Preparing a Component for Detection.

* cited by examiner

STRUCTURED FILM CONTAINING BETA-NUCLEATING AGENT AND METHOD OF MAKING THE SAME

BACKGROUND

Semi-crystalline polyolefins can have more than one kind of crystal structure. For example, isotactic polypropylene is known to crystallize into at least three different forms: alpha (monoclinic), beta (pseudohexangonal), and gamma (triclinic) forms. In melt-crystallized material the predominant form is the alpha or monoclinic form. The beta form generally occurs at levels of only a few percent unless certain heterogeneous nuclei are present or the crystallization has occurred in a temperature gradient or in the presence of shearing forces. The heterogeneous nuclei are typically known as beta-nucleating agents, which act as foreign bodies in a crystallizable polymer melt. When the polymer cools below its crystallization temperature, the loose coiled polymer chains orient themselves around the beta-nucleating agent to form beta-phase regions. The beta form of polypropylene is a metastable form, which can be converted to the more stable alpha form by thermal treatment and/or applying stress. It is known that micropores can be formed in various amounts when the beta-form of polypropylene is stretched under certain conditions. See, e.g., Chu et al., "Microvoid formation process during the plastic deformation of β-form polypropylene", *Polymer*, Vol. 35, No. 16, pp. 3442-3448, 1994, and Chu et al., "Crystal transformation and micropore formation during uniaxial drawing of β-form polypropylene film", *Polymer*, Vol. 36, No. 13, pp. 2523-2530, 1995.

In other technologies, articles with one or more structured surfaces are useful in a variety of applications (e.g., abrasive discs, assembly of automobile parts, and disposable absorbent articles). The articles may be provided as films that exhibit, for example, increased surface area, mechanical fastening structures, or optical properties.

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Mechanical fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

SUMMARY

The present disclosure provides a structured film of a semi-crystalline polyolefin that includes a beta-nucleating agent and a method of making the structured film. The structured film includes upstanding posts attached to a backing and may be useful, for example, as a mechanical fastening member.

The film may contain beta-spherulites, for example, in the upstanding posts and the backing when it is formed from a melt. When the film is stretched in at least one direction, for example, micropores are formed in the film backing. The upstanding posts are typically not affected by the stretching or are affected to a much lesser extent than the film backing and therefore generally have lower porosity than the film backing. The resulting stretched films typically have a unique visual appearance and feel and useful optical properties and mechanical properties. Unexpectedly, such properties of the film can be obtained at much lower stretch ratios than comparative flat films made of the same materials but having no upstanding posts.

In one aspect, the present disclosure provides a structured film comprising a semi-crystalline polyolefin and a beta-nucleating agent. The structured film has a backing and upstanding posts attached to the backing. The structured film may be a mechanical fastener, for example. At least a portion of the film typically includes beta-spherulites. In some embodiments, the backing is microporous while the upstanding posts have lower porosity than the backing.

In another aspect, the present disclosure provides a structured film of a semi-crystalline polyolefin having a backing and upstanding posts attached to the backing. Beta-spherulites of the semi-crystalline polyolefin are present in at least the upstanding posts. In some embodiments, the backing is microporous while the upstanding posts have lower porosity than the backing.

In another aspect, the present disclosure provides a method of making a structured film. In some embodiments, the method includes extruding a melt of a polyolefin and a beta-nucleating agent to provide a film backing, cooling at least a portion of the melt to a temperature sufficient to form beta-spherulites, and forming upstanding posts on the film backing to provide the structured film. In some embodiments, the method includes extruding a melt of a polyolefin and a beta-nucleating agent in the presence of a tool to provide the structured film having upstanding posts on a backing and cooling at least a portion of the structured film to a temperature sufficient to form beta-spherulites. In some embodiments, the method further includes stretching the structured film containing beta-spherulites to provide micropores in the backing. In some of these embodiments, the stretching is monoaxial. The same embodiments, the stretching is carried out to provide a total stretch ratio of up to 3:1.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The term "structured film" refers to a film with other than a planar or smooth surface.

The term "upstanding" refers to posts that protrude from the thermoplastic backing and includes posts that stand perpendicular to the backing and posts that are at an angle to the backing other than 90 degrees.

The terms "first" and "second" are used in this disclosure in their relative sense only. It will be understood that, unless otherwise noted, those terms are used merely as a matter of convenience in the description of one or more of the embodiments.

The term "loop-engaging" as used herein relates to the ability of a mechanical fastener element (i.e., hook element) to be mechanically attached to a loop material. Generally, hook elements with loop-engaging heads have a cap shape that is different from the shape of the post. The loop-engageability of hook elements may be determined and defined by using standard woven, nonwoven, or knit materials. A region of posts with loop-engaging caps generally will provide, in combination with a loop material, at least one of a higher peel strength, higher dynamic shear strength, or higher dynamic friction than a region of posts without loop-engaging caps.

The term "machine direction" (MD) as used herein denotes the direction of a running, continuous web of the semi-crystalline polyolefin useful for some embodiments of the method of making a structured film disclosed herein. When a patch of a structured film is a smaller portion cut from a continuous web, the machine direction generally corresponds to the length "L" of the structured film. As used herein, the terms machine direction and longitudinal direction are typically used interchangeably. The term "cross-direction" (CD) as used herein denotes the direction which is essentially perpendicular to the machine direction. When a patch of a structured film is a smaller portion cut from a continuous web, the cross direction corresponds to the width "W" of the structured film.

The term "microporous" refers to having multiple pores that have a largest dimension (in some cases, diameter) of up to 10 micrometers. Pore size is measured by measuring bubble point according to ASTM F-316-80.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1A:
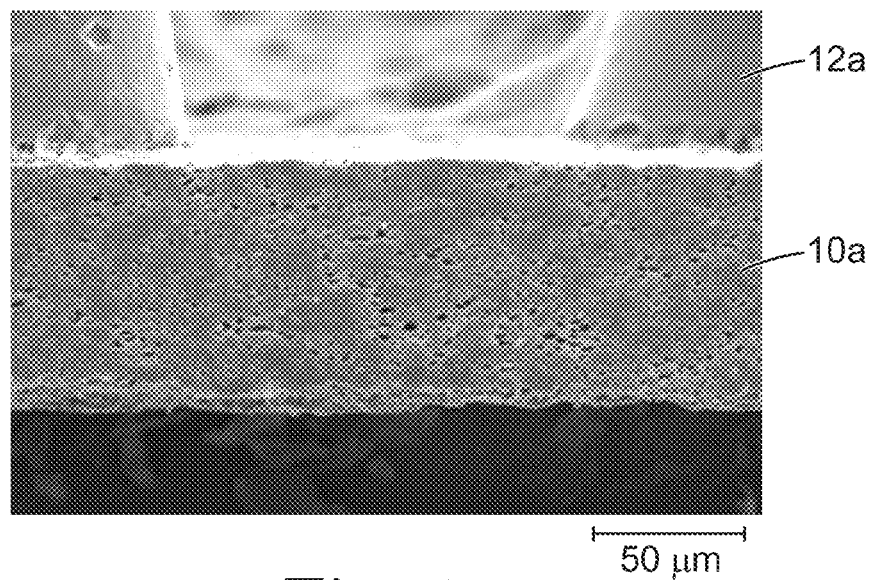
FIG. 1a is a scanning electron micrograph of a cross-section of the structured film of Example 4, which represents stretched embodiments of the structured film according to the present disclosure.
Figure 1B:
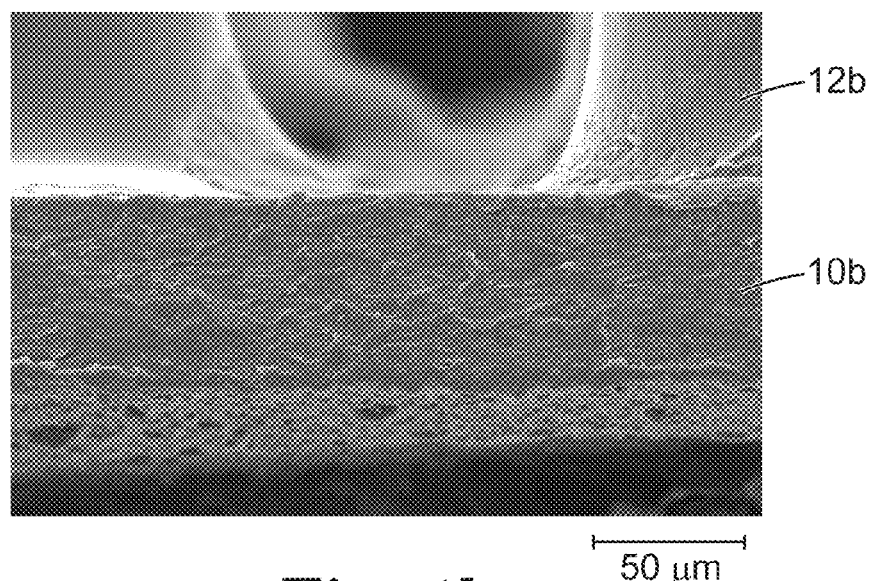
FIG. 1b is a scanning electron micrograph of a cross-section of the structured film of Comparative Example 4, which is a stretched structured film containing no beta-nucleating agent.

Structured films according to and/or made according to the present disclosure include a semi-crystalline polyolefin. Various polyolefins may be useful. Typically the semi-crystalline polyolefin comprises polypropylene. It should be understood that a semi-crystalline polyolefin comprising polypropylene may be a polypropylene homopolymer or a copolymer containing propylene repeating units. The copolymer may be a copolymer of propylene and at least one other olefin (e.g., ethylene or an alpha-olefin having from 4 to 12 or 4 to 8 carbon atoms). Copolymers of ethylene, propylene and/or butylenes may be useful. In some embodiments, the copolymer contains up to 90, 80, 70, 60, or 50 percent by weight of polypropylene. In some embodiments, the copolymer contains up to 50, 40, 30, 20, or 10 percent by weight of at least one of polyethylene or an alpha-olefin. The semi-crystalline polyolefin may also be part of a blend of thermoplastic polymers that includes polypropylene. Suitable thermoplastic polymers include crystallizable polymers that are typically melt processable under conventional processing conditions. That is, on heating, they will typically soften and/or melt to permit processing in conventional equipment, such as an extruder, to form a sheet. Crystallizable polymers, upon cooling their melt under controlled conditions, spontaneously form geometrically regular and ordered chemical structures. Examples of suitable crystallizable thermoplastic polymers include addition polymers, such as polyolefins. Useful polyolefins include polymers of ethylene (e.g., high density polyethylene, low density polyethylene, or linear low density polyethylene), an alpha-olefin (e.g., 1-butene, 1-hexene, or 1-octene), styrene, and copolymers of two or more such olefins. The semi-crystalline polyolefin may comprise mixtures of stereo-isomers of such polymers, e.g., mixtures of isotactic polypropylene and atactic polypropylene or of isotactic polystyrene and atactic polystyrene. In some embodiments, the semi-crystalline polyolefin blend contains up to 90, 80, 70, 60, or 50 percent by weight of polypropylene. In some embodiments, the blend contains up to 50, 40, 30, 20, or 10 percent by weight of at least one of polyethylene or an alpha-olefin.

In some embodiments, the structured film is made from a polymeric composition comprising a semi-crystalline polyolefin and having a melt flow rate in a range from 0.1 to 10 decigrams per minute, for example, 0.25 to 2.5 decigrams per minute.

Structured films according to and/or made according to the present disclosure include a beta-nucleating agent. The beta-nucleating agent may be any inorganic or organic nucleating agent that can produce beta-spherulites in a melt-formed sheet comprising polyolefin. Useful beta-nucleating agents include gamma quinacridone, an aluminum salt of quinizarin sulphonic acid, dihydroquinoacridin-dione and quinacridin-tetrone, triphenenol ditriazine, calcium silicate, dicarboxylic acids (e.g., suberic, pimelic, ortho-phthalic, isophthalic, and terephthalic acid), sodium salts of these dicarboxylic acids, salts of these dicarboxylic acids and the metals of Group IIA of the periodic table (e.g., calcium, magnesium, or barium), delta-quinacridone, diamides of adipic or suberic acids, different types of indigosol and cibantine organic pigments, quiancridone quinone, N',N'-dicyclohexyl-2,6-naphthalene dicarboxamide (available, for example, under the trade designation "NJ-Star NU-100" from New Japan Chemical Co. Ltd.), antraquinone red, and bis-azo yellow pigments. The properties of the extruded film are dependent on the selection of the beta nucleating agent and the concentration of the beta-nucleating agent. In some embodiments, the beta-nucleating agent is selected from the group consisting of gamma-quinacridone, a calcium salt of suberic acid, a calcium salt of pimelic acid and calcium and barium salts of polycarboxylic acids. In some embodiments, the beta-nucleating agent is quinacridone colorant Permanent Red E3B, which is also referred to as Q-dye. In some embodiments, the beta-nucleating agent is formed by mixing an organic dicarboxylic acid (e.g., pimelic acid, azelaic acid, o-phthalic acid, terephthalic acid, and isophthalic acid) and an oxide, hydroxide, or acid salt of a Group II metal (e.g., magnesium, calcium, strontium, and barium). So-called two component initiators include calcium carbonate combined with any of the organic dicarboxylic acids listed above and calcium stearate combined with pimelic acid. In some embodiments, the beta-nucleating agent is aromatic tri-carboxamide as described in U.S. Pat. No. 7,423,088 (Mäder et al.).

A convenient way of incorporating beta-nucleating agents into a semi-crystalline polyolefin useful for making a structured film disclosed herein is through the use of a concentrate. A concentrate is typically a highly loaded, pelletized polypropylene resin containing a higher concentration of nucleating agent than is desired in the final structured film. The nucleating agent is present in the concentrate in a range of 0.01% to 2.0% by weight (100 to 20,000 ppm), in some embodiments in a range of 0.02% to 1% by weight (200 to 10,000 ppm). Typical concentrates are blended with non-nucleated polyolefin in the range of 0.5% to 50% (in some embodiments, in the range of 1% to 10%) by weight of the total polyolefin content of the structured film. The concentration range of the beta-nucleating agent in the final structured film may be 0.0001% to 1% by weight (1 ppm to 10,000 ppm), in some embodiments, 0.0002% to 0.1% by weight (2 ppm to 1000 ppm). A concentrate can also contain other additives such as stabilizers, pigments, and processing agents.

The beta-nucleating agent employed in the present disclosure serves the important functions of inducing crystallization of the polymer from the molten state and enhancing the initiation of polymer crystallization sites so as to speed up the crystallization of the polymer. Thus, the nucleating agent may be a solid at the crystallization temperature of the polymer. Because the nucleating agent increases the rate of crystallization of the polymer, the size of the resultant polymer particles, or spherulites, is reduced.

The level of beta-spherulites in the semi-crystalline polyolefin can be determined, for example, using X-ray crystallography and Differential Scanning calorimetry (DSC). By DSC, melting points and heats of fusion of both the alpha phase and the beta phase can be determined in a structured film according to the present disclosure. For semi-crystalline polypropylene, the melting point of the beta phase is lower than the melting point of the alpha phase (e.g., by about 10 to 15 degrees Celsius). The ratio of the heat of fusion of the beta phase to the total heat of fusion provides a percentage of the beta-spherulites in a sample. In some embodiments, the level of beta-spherulites in at least a portion of the structured film according to the present disclosure is at least 10, 20, 25, 30, 40, or 50 percent, based on the total amount of alpha and beta phase crystals in the structured film. These levels of beta-spherulites may be found, for example, in the upstanding posts. Also, these levels of beta-spherulites may be found in the backing before the backing is stretched.

Additional ingredients may be included in the structured film according to the present disclosure, depending on the desired application. For example, surfactants, antistatic agents, ultraviolet radiation absorbers, antioxidants, organic or inorganic colorants, stabilizers, flame retardants, fragrances, and plasticizers may be included. It is also possible for the structured film to include an alpha-nucleating agent. Many of the beta-nucleating agents described above have a color. Additional colorants may be added, for example, in the form of a color concentrate or a colored master batch.

In some embodiments, the semi-crystalline polyolefin containing the beta-nucleating agent can be part of a multilayer or multi-component melt stream of thermoplastic materials. This can result in the upstanding posts formed at least partially from a different thermoplastic material than the one predominately forming the backing Various configurations of upstanding posts made from a multilayer melt stream are shown in U.S. Pat. No. 6,106,922 (Cejka et al.), for example. In embodiments wherein the structured film according to the present disclosure is a multilayer film or a multi-component film, it can be formed by any conventional method. A multilayer melt stream can be formed by a multilayer feedblock, such as that shown in U.S. Pat. No. 4,839,131 (Cloeren). A multi-component melt stream having domains or regions with different components could also be used. Useful multi-component melt streams could be formed by use of inclusion co-extrusion die or other known methods (e.g., that shown in U.S. Pat. No. 6,767,492 (Norquist et al.). Another useful process is described in U.S. Pat. No. 5,429,856 (Krueger et al.). This patent describes a polymer melt stream that is segmented into multiple substreams and then extruded into the center of another melt stream, which is then formed into a film. This co-extrusion method creates a film that has multiple segmented flows within a matrix of another polymer.

It is also possible for the structured film according to and/or made according to the present disclosure to by a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A die bar, or bars, at the exit region of the die segments two polymer flows using channels formed on the two outer faces of the die bar. The two sets of segmented polymer flows within these channels converge at a tip of the die bar where the two die bar faces meet. The segmented polymer flows are arranged so that when the two segmented polymer flows converge at the bar tip they form films that have alternating side-by-side zones of polymers. The use of two side-by-side die bars is also contemplated where two faces of adjacent die bars are joined and form a cavity that directs a third set of segmented polymer flows to the tip where the two die bars meet. The three segmented polymer flows converge and form an ABCABC side-by-side-by-side polymer flow. The die bars segment a single polymer flow into a series of laterally segmented flows along any given face of a die bar. A similar process that also includes co-extruding a continuous outer skin layer on one or both outer faces of the side-by-side co-extruded film as described in U.S. Pat. No. 6,669,887 (Hilston et al.) may also be useful.

In some embodiments, management of the flow of different polymer compositions into side-by-side lanes advantageously can be carried out using a single manifold die with a distribution plate in contrast to approaches that require multiple dies to achieve side-by-side co-extrusion. In some of these embodiments, the die comprises a first die cavity in a first die portion, a second die cavity in a second die portion, a distribution plate interposed between at least a portion (e.g., most or all) of the first die cavity and at least a portion (e.g., most or all) of the second die cavity. The distribution plate has a first side forming a boundary of the first die cavity, a second side forming a boundary of the second die cavity, a dispensing edge, a plurality of first extrusion channels, and a plurality of second extrusion channels. The first extrusion channels extend from entrance openings at the first die cavity to exit openings on the dispensing edge, and the second extrusion channels extend from entrance openings at the second die cavity to exit openings on the dispensing edge. The exit openings of the first extrusion channels and the exit openings of the second extrusion channels are disposed in alternating positions along the dispensing edge. Each of the first extrusion channels comprises two opposite side walls and a joining surface connecting the two opposite side walls, and the joining surface of at least some of the first extrusion channels is typically substantially parallel to the first side of the distribution plate. Further details about the die and the distribution plate can be found, for example, in International Patent Application Publication No. WO 2011/097436 (Gorman et al.), incorporated by reference herein in its entirety.

In some embodiments, the structured film is a coextruded film having side-by-side first and second lanes, wherein the first lanes comprise the semi-crystalline polyolefin and the beta-nucleating agent, and wherein the second lanes comprise a different polymer composition. In some embodiments, the structured film is a multilayer film having first and second layers, wherein the first layer comprises the semi-crystalline polyolefin and the beta-nucleating agent, and wherein the second layer comprises a different polymer composition. Suitable thermoplastic materials for the different polymer composition include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly (vinyl alcohol); ketones such as polyetheretherketone; polyphenylene sulfide; and mixtures thereof. In some embodiments, the different polymer composition (e.g., in the second lanes or second layer) includes an alpha nucleating agent (e.g., in polypropylene).

In some embodiments, the different polymer composition (e.g., in the second lanes or second layer) includes an elastomeric material. The term "elastomeric" refers to polymers from which films (0.002 to 0.5 mm thick) can be made that exhibit recovery from stretching or deformation. Exemplary elastomeric polymeric compositions which can be used in the segmented multicomponent polymeric films disclosed herein include thermoplastic elastomers such as ABA block copolymers, polyurethane elastomers, polyolefin elastomers (e.g., metallocene polyolefin elastomers), polyamide elastomers, ethylene vinyl acetate elastomers, and polyester elastomers. An ABA block copolymer elastomer generally is one where the A blocks are polystyrenic, and the B blocks are conjugated dienes (e.g., lower alkylene dienes). The A block is generally formed predominantly of substituted (e.g., alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, for example, in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastomers can be blended with block copolymer elastomers provided that the elastomeric properties are not adversely affected. Many types of thermoplastic elastomers are commercially available, including those from BASF under the trade designation "STYROFLEX", from Shell Chemicals under the trade designation "KRATON", from Dow Chemical under the trade designation "PELLETHANE" or "ENGAGE", from DSM under the trade designation "ARNITEL", from DuPont under the trade designation "HYTREL", and more. The thermoplastic elastomers, including tetrablock styrene/ethylene-propylene/styrene/ethylene-propylene, described in U.S. Pat. No. 6,669,887 (Hilston et al.) may also be useful.

In the structured film according to and/or made according to the present disclosure, the backing and the upstanding posts are typically integral (that is, formed at the same time as a unit, unitary). The backing is typically in the form of a sheet or web that may have an essentially uniform thickness with the upstanding posts directly attached to the backing. In the method of making a structured film according to the present disclosure, a melt of a polyolefin and a beta-nucleating agent is extruded to provide a film backing. The method includes cooling at least a portion of the melt to a temperature sufficient to form beta-spherulites (e.g., a temperature in a range from 60° C. to 120° C. or 90° C. to 120° C.) and forming upstanding posts on the film backing to provide the structured film. In some of these embodiments, forming the upstanding posts on the film backing is carried out after cooling at least a portion of the melt (e.g., by exposing the film to a tool and heating). In other embodiments, a melt of a polyolefin and a beta-nucleating agent is extruded in the presence of a tool to provide the structured film having upstanding posts on a backing for at least a portion of the film. The structured film is then cooled to a temperature sufficient to form beta-spherulites.

Upstanding posts on a backing can be made, for example, by conventional extrusion through a die and cast molding techniques. In some embodiments, a polyolefin composition containing the beta-nucleating agent is fed onto a continuously moving mold surface with cavities having the inverse shape of the upstanding posts. The polyolefin composition can be passed between a nip formed by two rolls or a nip between a die face and roll surface, with at least one of the rolls having the cavities (i.e., at least one of the rolls is a tool roll). Pressure provided by the nip forces the resin into the cavities. In some embodiments, a vacuum can be used to evacuate the cavities for easier filling of the cavities. The nip has a gap that is typically large enough such that a coherent backing is formed over the cavities. The mold surface and cavities can optionally be air or water cooled to a temperature sufficient to form beta-spherulites (e.g., a temperature in a range from 60° C. to 120° C. or 90° C. to 120° C.). In these embodiments, cooling at least a portion of the structured film to a temperature sufficient to form beta-spherulites is carried out in the presence of the tool that forms the upstanding posts.

The integrally formed backing and upstanding posts can then be stripped from the mold surface such as by a stripper roll.

Suitable tool rolls can be made, for example, by forming (e.g., by computer numerical control with drilling, photo etching, using galvanic printed sleeves, laser drilling, electron beam drilling, metal punching, direct machining, or lost wax processing) a series of holes having the inverse shape of the upstanding posts into the cylindrical face of a metal mold or sleeve. Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). The exposed surface of the mold, sleeve, plate, or wire may be coated to impart surface properties such as increased wear resistance, controlled release characteristics, and controlled surface roughness. The coating, if present, is typically selected so that the adhesion of the polyolefin composition to the tool roll is less than the cohesion of the polyolefin composition at the time of the removal of the thermoplastic backing from the tool roll.

Another exemplary method for forming a backing with upstanding posts includes using a flexible mold belt defining an array of upstanding post-shaped cavities as described in U.S. Pat. No. 7,214,334 (Jens et al.). The mold belt is trained about first and second rolls. A source of molten polyolefin composition can be arranged to deliver the polyolefin composition to the mold belt. The apparatus is constructed to force the plastic resin into the post-shaped cavities of the belt under pressure in a gap to mold the array of upstanding posts while forming the backing.

Figure 2A:
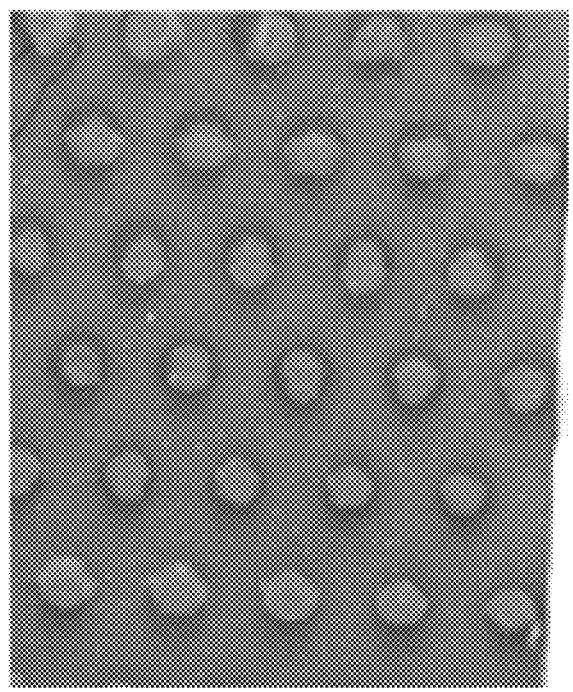
FIG. 2a is an optical microscope image of a top view of an exemplary structured film according to the present disclosure where the film has not been stretched.
Figure 2B:
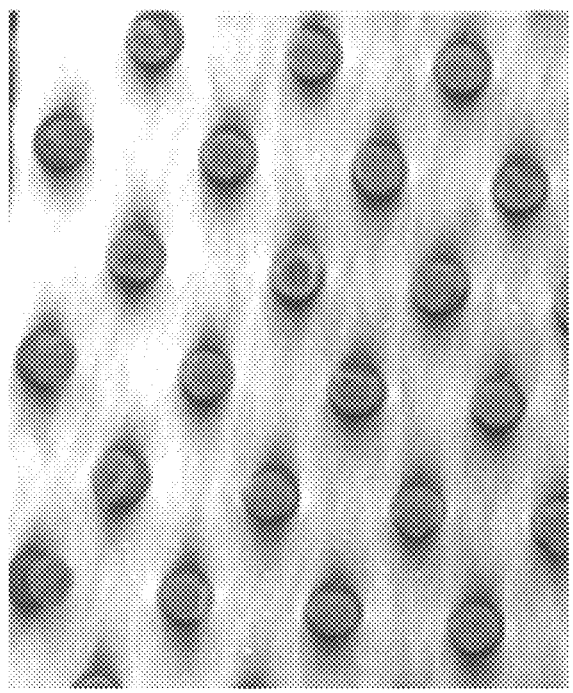
FIG. 2b is an optical microscope image of a top view of an exemplary structured film according to the present disclosure where the film has been stretched.
Figure 5A:
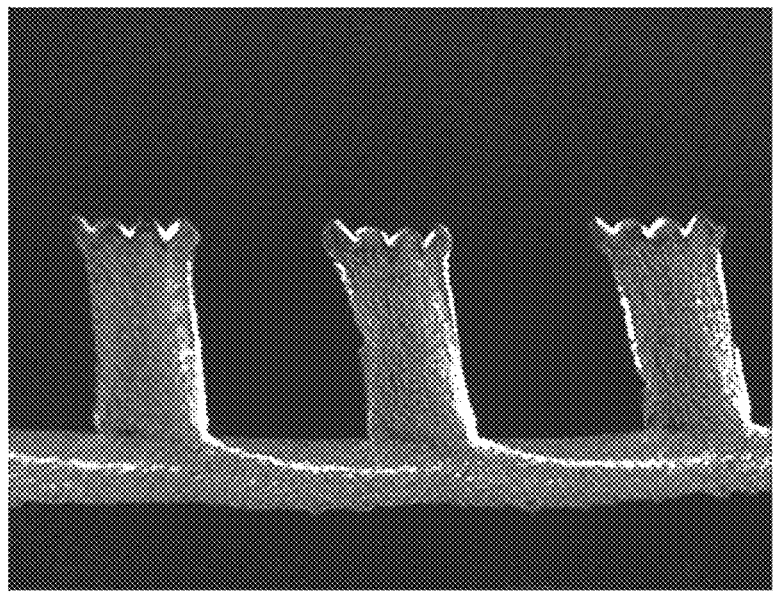
FIGS. 5a and 5b are optical microscope images of Comparative Examples 1 and 2, respectively, using a retardance imaging system to evaluate birefringence.
Figure 5B:
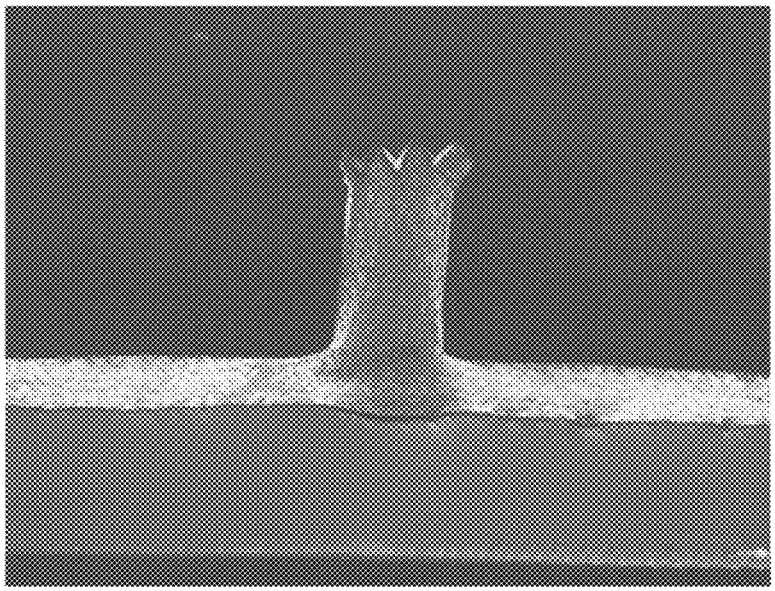
Figure 6A:
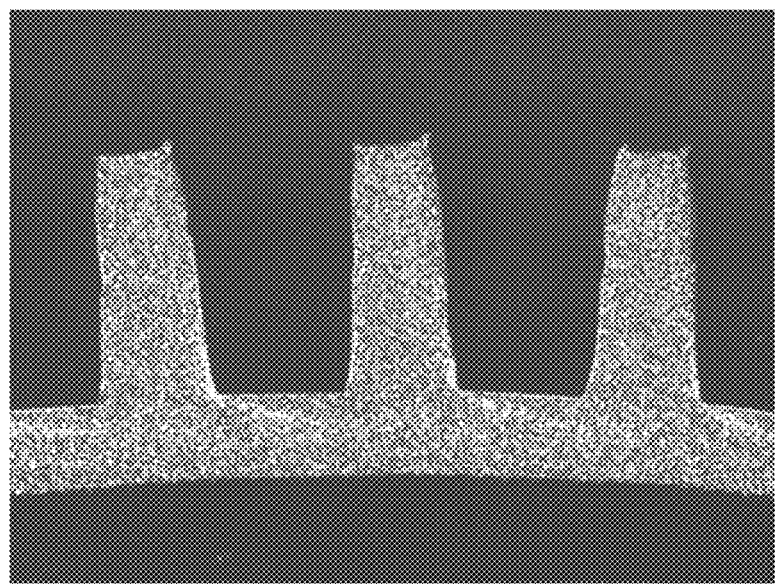
FIGS. 6a and 6b are optical microscope images of Examples 5 and 6, respectively, using a retardance imaging system to evaluate birefringence.
Figure 6B:
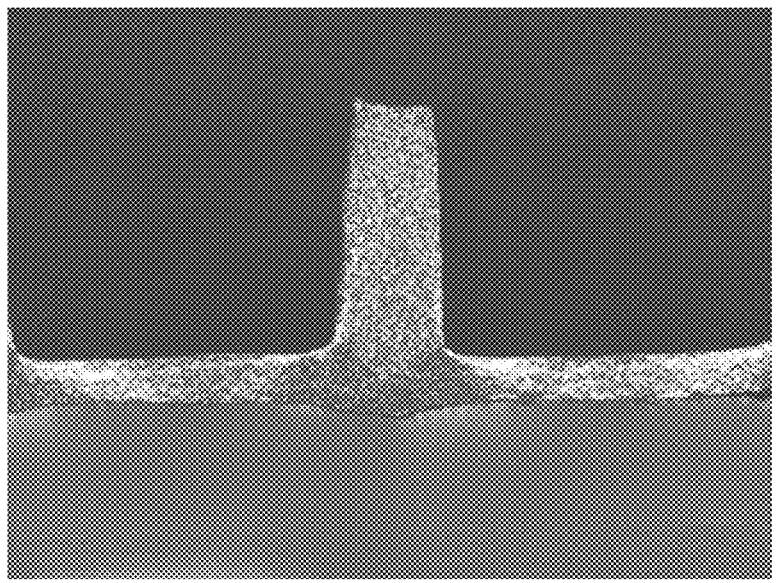

The upstanding posts, which may be made, for example, by any of the methods described above, have a base portion attached to a first surface of the backing and a free end distal from the backing as illustrated in FIGS. 5a, 5b, 6a, and 6b. The first surface of the backing is defined by the length and width dimensions of the backing as shown in FIGS. 2a and 2b, and the thickness dimension of the backing is the smallest dimension as shown in FIGS. 6a and 6b.

The upstanding posts, which may be made, for example, by any of the methods described above, may have a shape that tapers, for example, from base portion attached to the backing to a distal tip. The base portion may have a larger width dimension than the distal tip, which may facilitate the removal of the post from the mold surface in the methods described above.

In some embodiments, the distal tips of the upstanding posts that are formed according to any of the above methods are deformed to form caps with loop-engaging overhangs. A combination heat and pressure, sequentially or simultaneously, may be used to deform the distal tips of the posts to form caps. In some embodiments, deforming comprises contacting the distal tips with a heated surface. The heated surface may be a flat surface or a textured surface such as that disclosed in U.S. Pat. No. 6,708,378 (Parellada et al.) or U.S. Pat. No. 5,868,987 (Kampfer et al.). In some embodiments, wherein the backing with upstanding posts is a web of indefinite length, the deforming comprises moving the web in a first direction through a nip having a heated surface member and an opposing surface member such that the heated surface member contacts the distal tips. In these embodiments, the heated surface may be, for example, a capping roll. In some embodiments, the surface used to contact the distal tips is not heated. In these embodiments, the deformation is carried out with pressure and without heating. In some embodiments, the heated surface may be a heated roll opposite a curved support surface forming a variable nip having a variable nip length as described, for example, in U.S. Pat. No. 6,368,097 (Miller et al.). The curved support surface may curve in the direction of the heated roll, and the heated roll may include a feeding mechanism for feeding the backing with upstanding posts through the variable nip to compressively engage the web between the heated roll and the support surface.

Another suitable method for forming a backing with upstanding posts attached to the backing is profile extrusion, which is described, for example, in U.S. Pat. No. 4,894,060 (Nestegard). In this method a flow stream of the polyolefin composition containing the beta-nucleating agent is passed through a patterned die lip (e.g., cut by electron discharge machining) to form a web having downweb ridges. The ridges are then transversely sliced at spaced locations along the extension of the ridges to form upstanding posts with a small separation caused by the cutting blade. It should be understood that "upstanding posts" do not include such ridges before they are cut. However, the patterned die lip may be considered a tool to provide the structured film having upstanding posts on a backing. The separation between the upstanding posts is then increased by stretching the film in the direction of the ridges using one of the stretching methods described below. The ridges themselves would also not be considered "loop-engaging" because they would not be able to engage loops before they are cut and stretched. In some embodiments, methods according to the present disclosure do not include cutting ribs (e.g., made by profile extrusion).

In addition to the continuous methods described above, it is also envisioned that structured films comprising backings with upstanding posts can be prepared using batch processes (e.g., single piece injection molding). The backing may have any suitable dimension, but length (L) and width (W) dimensions of at least 10 cm may be useful.

In the structured film according to and/or made according to the present disclosure, the upstanding posts, which may be made, for example, by any of the methods described above, may have a variety of cross-sectional shapes. For example, the cross-sectional shape of the post may be a polygon (e.g., square, rectangle, hexagon, or pentagon), which may be a regular polygon or not, or the cross-sectional shape of the post may be curved (e.g., round or elliptical).

In the structured film according to and/or made according to the present disclosure, the backing may have a variety of thicknesses. For example, the initial thickness (i.e., before any stretching) of the backing may be up to about 750, 500, 400, 250, or 150 micrometers, depending on the desired application. In some embodiments, the initial thickness of the backing is at least about 50, 75, or 100 micrometers, depending on the desired application. In some embodiments, the initial thickness of the backing is in a range from 50 to about 225 micrometers, from about 75 to about 200 micrometers, or from about 100 to about 150 micrometers. The backing may have an essentially uniform cross-section, or the backing may have additional structure beyond what is provided by the upstanding posts, which may be imparted, for example, by at least one of the forming rolls described above.

In some embodiments, the upstanding posts have a maximum height (above the backing) of up to 3 millimeters (mm), 1.5 mm, 1 mm, or 0.5 mm and, in some embodiments, a minimum height of at least 0.05 mm, 0.075 mm, 0.1 mm, or 0.2 mm. In some embodiments, the posts have aspect ratio (that is, a ratio of height over a width dimension) of at least about 2:1, 3:1, or 4:1. The aspect ratio may be, in some embodiments, up to 10:1. For posts with caps, the caps are typically larger in area than the cross-sectional area of the posts. A ratio of a width dimension of the cap to the post measured just below the cap is typically at least 1.5:1 or 3:1 and may be up to 5:1 or greater. The capped posts are typically shorter than the posts before capping. In some embodiments, the capped posts have a height (above the backing) of at least 0.025 mm, 0.05 mm, or 0.1 mm and, in some embodiments, up to 2 mm, 1.5 mm, 1 mm, or 0.5 mm. The posts, which may be capped or not, may have a cross-section with a maximum width dimension of up to 1 (in some embodiments, up to 0.75, 0.5, or 0.45) mm. In some embodiments, the posts have a cross-section with a width dimension between 10 μm and 250 μm. The term "width dimension" should be understood to include the diameter of a post with a circular cross-section. When the post has more than one width dimension (e.g., in a rectangular or elliptical cross-section shaped post or a post that tapers as described above), the aspect ratio described herein is the height over the largest width dimension.

The upstanding posts are typically spaced apart on the backing. The term "spaced-apart" refers to posts that are formed to have a distance between them. The bases of "spaced-apart" posts, where they are attached to the backing, do not touch each other before or after stretching the backing when the backing is in an unbent configuration. In the structured film according to and/or made according to the present disclosure, the spaced-apart upstanding posts have an initial density (i.e., before any stretching of the film) of at least 10 per square centimeter ($cm^2$) (63 per square inch $in^2$). For example, the initial density of the posts may be at least 100/$cm^2$ (635/$in^2$), 248/$cm^2$ (1600/$in^2$), 394/$cm^2$ (2500/$in^2$), or 550/$cm^2$ (3500/$in^2$). In some embodiments, the initial density of the posts may be up to 1575/$cm^2$ (10000/$in^2$), up to about 1182/$cm^2$ (7500/$in^2$), or up to about 787/$cm^2$ (5000/$in^2$). Initial densities in a range from 10/$cm^2$ (63/$in^2$) to 1575/$cm^2$ (10000/$in^2$) or 100/$cm^2$ (635/$in^2$) to 1182/$cm^2$ (7500/$in^2$) may be useful, for example. The spacing of the upstanding posts need not be uniform.

In some embodiments, the method of making a structured film according to the present disclosure includes stretching the backing to provide micropores in the backing Without wanting to be bound by theory, it is believed that when the film is stretched in at least one direction, for example, the semi-crystalline polypropylene converts from the beta-crystalline structure to the alpha-crystalline structure in the backing, and micropores are formed in the film backing. The upstanding posts are typically not affected by the stretching or are affected to a much lesser extent than the film backing and therefore retain beta-crystalline structure. A scanning electron microscope image of a cross-section of structured film according to and/or made according to the present disclosure after it is stretched is shown in FIG. 1a. FIG. 1a shows that the backing 10a is porous while the upstanding posts 12a are not microporous.

The resulting stretched films can have several unique properties. For example, the micropores formed in the backing along with stress-whitening can provide an opaque, white film while the upstanding posts are transparent. The visible contrast between the backing and the upstanding posts may be enhanced by the presence of a colorant in the structured film. Colorants may be added to a polyolefin before film formation, for example, using a color concentrate as described above. The colored backings also undergo stress-whitening and microvoiding upon stretching, and these changes are manifested typically as a visible reduction in intensity of the color of the backing. As a result, the stretched backing may be a pastel color while the intensity of the color of the upstanding posts is maintained. If a low enough concentration of the color concentrate, for example, is used, the resulting stretched film may have an appearance of an almost white backing with colored upstanding posts. The change in appearance between a structured film according to the present disclosure before stretching and after stretching is shown in FIGS. 2a and 2b, respectively. The difference in appearance between the backing and the upstanding posts in the stretched structured film as shown in FIG. 2b provides unique and pleasing aesthetics.

In some embodiments of the method of making a structured film according to the present disclosure, stretching the structured film containing beta-spherulites provides an increase in opacity in the structured film of at least ten percent. In some embodiments, this stretching provides at increase in opacity of at least 15, 20, 25, or 30 percent. The increase in opacity may be, for example, up to 90, 85, 80, 75, 70, 65, 60, 55, or 50 percent. The initial opacity in the structured film is affected, for example, by the thickness of the film. Stretching the film typically results in a decrease in thickness, which would typically lead to a decrease in opacity. However, in the structured film disclosed herein, the stress whitening and micropore formation leads to an increase in opacity. In these embodiments, opacity is measured using a spectrophotometer with the "L" value measured separately against a black background and against a white background, respectively. The opacity is calculated as (L measured against the black background/L measured against the white background) times 100. The "L" value is one of three standard parameters in the CIELAB color space scale established by the International Commission on Illumination. "L" is a brightness value, ranging from 0 (black) to 100 (highest intensity). Further details about the test method are provided in the Examples, below. A percentage change in opacity that results from stretching the structured film is calculated by [(opacity after stretching−opacity before stretching)/opacity before stretching]times 100.

In some embodiments of the method of making a structured film according to the present disclosure, stretching the structured film containing beta-spherulites provides a decrease in the grayscale value of the film of at least twenty percent. In some embodiments, this stretching provides a decrease in a grayscale value of at least 25, 30, 40, or 50 percent. The decrease in grayscale value may be, for example, up to 90, 85, 80, 75, 70, 65, or 60 percent. For these embodiments, the grayscale value is measured in transmission mode using the method described in the Example section, below. Stretching a film typically results in a decrease in thickness, which would typically lead to an increase in the grayscale value measured in transmission mode. However, in the structured films disclosed herein, the stress whitening and micropore formation leads to decrease in transmission mode grayscale values. A percentage change in grayscale value that results from stretching the film is calculated by [(grayscale value after stretching−grayscale value before stretching)/grayscale value before stretching]times 100.

In some embodiments of the structured film according to the present disclosure, the microporous structured film has a grayscale value of up to 40 (in some embodiments, up to 35, 30, 25, 20 or 15). For these embodiments, the grayscale value is measured in transmission mode using the method described in the Examples, below. The grayscale values for the microporous structured films disclosed herein are comparable or better than those achieved for polyolefin films of similar composition but incorporating conventional amounts of IR blocking agents such as titanium dioxide.

The opacity and grayscale measurement of the structured film relate to its ability to transmit light. As used herein, the term "light" refers to electromagnetic radiation, whether visible to the unaided human eye or not. Ultraviolet light is light having a wavelength in a range from about 250 nanometers (nm) to 380 nm. Visible light is light having a wavelength in a range from 380 nanometers (nm) to 700 nm. Infrared light has a wavelength in a range from about 700 nm to 300 micrometers. After the structured film according to the present disclosure has been stretched, it has decreased transmission to ultraviolet, visible, and infrared light. The micropores in the stretched structured film tend to scatter light in the ultraviolet, visible, and infrared ranges.

In some embodiments of the structured film according to and/or made according to the present disclosure, the microporous structured film has a percent transmittance in a range from 8 percent to 60 percent in a wavelength range of 250 nm to 2250 nm. Before stretching, the same film may have a percent transmittance in a range from 40 percent to about 80 percent in the same wavelength range. In some embodiments, as shown in the Examples, below, an exemplary structured film including a beta-nucleating agent has a percent transmittance that decreases at least 25% and up to 60%, 70%, or 75% upon stretching depending on the degree of stretching, the stretch temperature, and the wavelength range (e.g., ultraviolet, visible, or infrared). In some embodiments, the microporous structured film has a percent reflectance in a range from about 20 percent to about 80 percent in a wavelength range of 250 nm to 2250 nm. Before stretching, the same film may have a percent reflectance in a range from 3 percent to about 30 percent in the same wavelength range. In some embodiments, as shown in the Examples, below, an exemplary structured film including a beta-nucleating agent has a percent reflectance that increases at least 55% or 80% and up to 150%, 200%, or 250% upon stretching depending on the degree of stretching, the stretch temperature, and the wavelength range. That is, the percent reflectance has a percent increase of at least 55% or 80% and up to 150%, 200%, or 250% upon stretching.

The ability of the stretched structured films to block the transmission of light (e.g., by scattering) allows them to be detected in inspection systems that rely upon shining a light onto a substrate and detecting the amount of light received from the area of the irradiated substrate. For example, in the manufacture of a composite article, the presence or position of a stretched structured film disclosed herein or a portion thereof incorporated into the composite article can be detected because of its ability to block ultraviolet, visible, and/or infrared light. The composite article may be, for example, a disposable absorbent article, and the structured film may be a mechanical fastening patch to be incorporated into the disposable absorbent article. The response of the mechanical fastening patch to irradiation by at least one of ultraviolet, visible, or infrared light is evaluated. Subsequently, during manufacturing a composite article can be irradiated, and at least one of the ultraviolet, visible, or infrared radiation received from the irradiated composite article can be detected and analyzed for the predefined response of the mechanical fastening patch. The position of the mechanical fastening patch can be determined using an image analyzer that can detect predefined variations in grayscale values, for example, that correspond to the positions of the mechanical fastening patch and other components. The ability of the stretched structured film disclosed herein to scatter infrared light allows it to be detected even when it is between other layers of materials in the composite article. For more information regarding methods of detecting microporous films in a composite article, see U.S. Pat. App. Pub. No. 2013/0147076 (Chandrasekaran et al.)

While detection of the presence or position of a component using an inspection system that relies on detection of infrared light has been described previously, the component contained an IR blocking agent that could either absorb or reflect infrared light. See, e.g., U.S. Pat. No. 6,927,857 (Koele et al.). Surprisingly, the stretched structured film disclosed herein can block infrared radiation in equivalent or greater amounts than films prepared from similar polyolefin materials and loaded with IR blocking agents. In some embodiments, the structured film disclosed herein is essentially free of an IR blocking agent (e.g., an absorbing or reflecting agent). In some embodiments, the structured film disclosed herein is essentially free of an IR absorbing agent. The structured film that is "essentially free of" an IR absorbing agent may have no IR absorbing agent or may have an IR absorbing agent in an amount of less than 1, 0.5, or 0.01 percent by weight or less than 10 ppm or 10 ppb. In some embodiments, the structured film disclosed herein is essentially free of an IR reflecting or scattering agent. The structured film that is "essentially free of" an IR reflecting or scattering agent may have no IR reflecting or scattering agent or may have an IR reflecting or scattering agent in an amount of less than 2, 1.5, 1, or 0.5 percent by weight. In some of these embodiments, the structured film is essentially free of an IR reflecting or scattering agent selected from the group consisting of titanium dioxide, barium sulfate, magnesium oxide, calcium carbonate, polytetrafluoroethylene micro beads, and polyolefin microbeads.

When micropores are formed in the backing of the stretched structured film disclosed herein, the density of the film decreases. The resulting low-density stretched structured film feels softer to the touch than films having comparable thicknesses but higher densities. The density of the film can be measured using conventional methods, for example, using helium in a pycnometer. In some embodiments of the method of making a structured film according to the present disclosure, stretching the structured film containing beta-spherulites provides a decrease in density in the structured film of at least three percent. In some embodiments, this stretching provides at decrease in density of at least 5 or 7.5 percent. For example, the stretching provides at decrease in density in a range from 3 to 15 percent or 5 to 10 percent. A percentage change in density that results from stretching the structured film is calculated by [(density before stretching−density after stretching)/density before stretching]times 100. The softness of the film can be measured, for example, using Gurley stiffness as described in the Examples, below.

Stretching the structured film disclosed herein can be carried out on a web biaxially or monoaxially. Biaxial stretching means stretching in two different directions in the plane of the backing. Typically, but not always, the first direction is the longitudinal direction "L", and the second direction is the width direction "W". Biaxial stretching can be performed sequentially by stretching the thermoplastic backing, for example, first in one of the first or second direction and subsequently in the other of the first or second direction. Biaxial stretching can also be performed essentially simultaneously in both directions. Monoaxial stretching refers to stretching in only one direction in the plane of the backing. Typically, monoaxial stretching is performed in one of the "L" or "W" direction but other stretch directions are also possible.

While unstructured films comprising polypropylene with beta-spherulites have been demonstrated to become microporous and increase in opacity upon stretching, high stretch ratios are reported to be required to achieve a desirable level of porosity or opacity. In some cases, stretch ratios exceeding 5:1, 10:1 or even 20:1 are reported. See, e.g., U.S.

Pat. No. 6,815,048 (Davidson et al.), U.S. Pat. Appl. Pub. No. 2006/0177632 (Jacoby), and UK Pat. App. GB 2323325, published Sep. 23, 1998. In some cases, biaxial stretching is preferred. Unexpectedly, a structured film comprising a semi-crystalline polyolefin and a beta-nucleating agent, the structured film comprising a backing and upstanding posts attached to the backing as disclosed herein, can be stretched at relatively low stretch ratios, and in some cases, in only one direction, to achieve high levels of porosity and opacity. As shown in the Examples below, a structured film according to the present disclosure can be stretched monoaxially at a stretch ratio of 2:1 to provide a film having lower density and higher opacity than a flat film made using the same materials by the same method except having no upstanding posts.

High levels of porosity and opacity are achieved with low stretch ratios even in the absence of other cavitating agents such as calcium carbonate or diluents that phase separate from the semi-crystalline polyolefin. Accordingly, in some embodiments, structured films according to and/or made according to the present disclosure are substantially free of a diluent that phase separates below the melting temperature of the semi-crystalline polyolefin. Such diluents include hydrocarbon waxes, petroleum jelly, mineral oil, mineral spirits, dioctylphthalate, and paraffin wax. In some embodiments, structured films according to and/or made according to the present disclosure are substantially free of a cavitating agent. The term "substantially free of" when referring to a diluent or cavitating agent means that any diluent or cavitating agent in the structured film may be present at a level of up to 5, 2.5, 1, 0.5, or 0.1 percent by weight, based on the total weight of the structured film. "Substantially free of" diluents or cavitating agent includes "free of" diluents or cavitating agents.

In some embodiments of the method disclosed herein, the stretching increases at least one of the backing's length ("L") or width ("W") at least 1.2 times (in some embodiments, at least 1.5, 2, or 2.5 times). In some embodiments, the stretching increases both of the backing's length ("L") and width ("W") at least 1.2 times (in some embodiments, at least 1.5, 2, or 2.5 times). In some embodiments, the stretching increases at least one of the backing's length ("L") or width ("W") up to 5 times (in some embodiments, up to 2.5 times). In some embodiments, the stretching increases both of the backing's length ("L") and width ("W") up to 5 times (in some embodiments, up to 2.5 times). It has unexpectedly been found that even monoaxial stretching at a stretch ratio of up to 2.5, 2.25, 2.2, or even 2 can provide high levels of porosity and opacity even in the absence of other cavitating agents such as calcium carbonate.

Structured films according to the present disclosure have unique birefringence properties when compared to semi-crystalline polyolefin films made without beta-nucleating agents. Birefringence refers to a property of a material having different effective indexes of refraction in different directions. In the present application, birefringence is evaluated with a retardance imaging system available from Lot-Oriel GmbH & Co., Darmstadt, Germany, under the trade designation "LC-POLSCOPE" on a microscope available from Leica Microsystems GmbH, Wetzlar, Germany, under the trade designation "DMRXE" and a digital CCD color camera available from Qlmaging, Surrey, BC, Canada, under the trade designation "RETIGA EXi FAST 1394". The microscope is equipped with a 546.5 nm interference filter obtained from Cambridge Research & Instrumentation, Inc., Hopkinton, Mass., and 10×/0.25 objective. For the structured films disclosed herein, as shown in the Examples below, birefringence in the backing is not significantly changed by stretching while in films of semi-crystalline polypropylene not containing a beta nucleating agent, the birefringence measurement in the backing increases after stretching. The birefringence measurement in the posts is not significantly changed by stretching in both the structured film disclosed herein and in films of semi-crystalline polypropylene not containing a beta nucleating agent.

Before stretching, the backing and the upstanding posts of the structured films disclosed herein both exhibit areas of both positive and negative birefringence, as evidenced by the speckled appearance (i.e., light and dark regions) in FIGS. 6a and 6b, which are images of Examples 5 and 6, respectively, described below. After stretching, the film backing has a less speckled appearance, which is evident when comparing FIGS. 6b to 6a. For a comparative film of semi-crystalline polypropylene not containing a beta nucleating agent, before stretching the backing and the upstanding posts both exhibit a predominantly homogeneous pattern of positive birefringence as shown in FIG. 5a, which is an image of Comparative Example 1, described below. A speckled pattern is not observed. After stretching, as shown in FIG. 5b, which is an image of Comparative Example 2, the film backing has stretch induced birefringence as evidenced by the lighter appearance of the film backing.

In general, when a thermoplastic film is monoaxially or biaxially stretched at a temperature below the melting point of the thermoplastic material, particularly at a temperature below the line drawing temperature of the film, the thermoplastic film may stretch non-uniformly, and a clear boundary is formed between stretched and unstretched parts. This phenomenon is referred to as necking or line drawing. However, substantially the entire thermoplastic backing is stretched uniformly when it is stretched to a sufficiently high degree. The stretch ratio at which this occurs is referred to as the "natural stretch ratio" or "natural draw ratio." Stretching above the natural stretch ratio is understood to provide significantly more uniform properties or characteristics such as thickness, tensile strength, and modulus of elasticity. For any given thermoplastic backing and stretch conditions, the natural stretch ratio is determined by factors such as the composition of the thermoplastic resin forming the thermoplastic backing, the morphology of the formed thermoplastic backing due to quenching conditions on the tool roll, for example, and temperature and rate of stretching. Furthermore, for biaxially stretched thermoplastic backings, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in the first direction and one in the second direction) which result in the natural stretch ratio. The term "stretch ratio" refers to ratio of a linear dimension of a given portion of the thermoplastic backing after stretching to the linear dimension of the same portion before stretching. The natural stretch ratio of the most common crystalline form of polypropylene, the alpha form, has been reported to be about 6:1.

We have found that stretching a structured film having mainly the alpha form of polypropylene and no beta nucleating agent at low stretch ratios in the range of 2:1 to 2.5:1 results in a film with a blotchy appearance while stretching a comparable structured film including beta-spherulites at these low stretch ratios results in a film with a uniform appearance. The uniform appearance of the film can be achieved even when the upstanding posts are the only structural elements of the film. In other words, the film does not require any stretch limiting formations as described in U.S. Pat. No. 6,582,642 (Buzzell et al.).

Other differences between structured films having mainly the alpha form of polypropylene and no beta nucleating agent and the structured films according to the present disclosure have been observed, as described in detail in the Examples, below. For example, the neck down at a stretch ratio of 2:1 of a structured film having mainly the alpha form of polypropylene and no beta nucleating agent is in a range from about 15 percent to 20 percent. In contrast, the neck down at a stretch ratio of 2:1 of a structured film comprising a semi-crystalline polyolefin and a beta-nucleating agent according to the present disclosure is about 10 percent. Also, the reduction in film thickness upon stretching at a stretch ratio of 2:1 is less for a structured film according to the present disclosure than for a structured film having mainly the alpha form of polypropylene and no beta nucleating agent. The thickness of the backing after stretching a structured film according to the present disclosure may be, for example, in a range from 5 to 200 μm, 10 to 100 μm, or 30 to 70 μm.

Stretching the structured film in a method according to the present disclosure can be carried out in a variety of ways. When the structured film is a web of indefinite length, for example, monoaxial stretching in the machine direction can be performed by propelling the structured film over rolls of increasing speed. A versatile stretching method that allows for monoaxial, sequential biaxial, and simultaneous biaxial stretching of the structured film employs a flat film tenter apparatus. Such an apparatus grasps the thermoplastic web using a plurality of clips, grippers, or other film edge-grasping means along opposing edges of the structured film in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany.

Stretching the structured film is typically performed at elevated temperatures, for example, up to 150° C. Heating the structured film may allow the backing to be more flexible for stretching. Heating can be provided, for example, by IR irradiation, hot air treatment or by performing the stretching in a heat chamber. In some embodiments, heating is only applied to the second surface of the backing (i.e., the surface opposite the first surface from which the upstanding posts project) to minimize any damage to the upstanding posts that may result from heating. For example, in these embodiments, only rollers that are in contact with the second surface of the backing are heated. In some embodiments, stretching the structured film is carried out at a temperature range from 50° C. to 130° C. As shown in the Examples, below, levels of porosity and opacity in the stretched structured films disclosed herein have been found to increase as the stretch temperature decreases. In some embodiments, the temperature range is from 50° C. to 110° C., 50° C. to 90° C., or 50° C. to 80° C. In some embodiments, stretching at lower temperatures may be possible, for example, in a range from 25° C. to 50° C. It has unexpectedly been found that stretching the structured films disclosed herein can be carried out at lower temperatures than flat films including a beta-nucleating agent previously described. For example, structured films of a semi-crystalline polyolefin containing a beta-nucleating agent can even be stretched at a temperature of up to 70° C. (e.g., in a range from 50° C. to 70° C. or 60° C. to 70° C.).

After stretching the density of the upstanding posts is less than the initial density of the upstanding posts. In some embodiments of the structured film according to and/or made according to the present disclosure, the upstanding posts have a density after stretching of at least 2 per square centimeter ($cm^2$) (13 per square inch $in^2$). For example, the density of the posts after stretching may be at least $62/cm^2$ ($400/in^2$), $124/cm^2$ ($800/in^2$), $248/cm^2$ ($1600/in^2$), or $394/cm^2$ ($2500/in^2$). In some embodiments, the density of the posts after stretching may be up to about $1182/cm^2$ ($7500/in^2$) or up to about $787/cm^2$ ($5000/in^2$). Densities after stretching in a range from $2/cm^2$ ($13/in^2$) to $1182/cm^2$ ($7500/in^2$) or $124/cm^2$ ($800/in^2$) to $787/cm^2$ ($5000/in^2$) may be useful, for example. Again, the spacing of the posts need not be uniform.

Figure 4A:
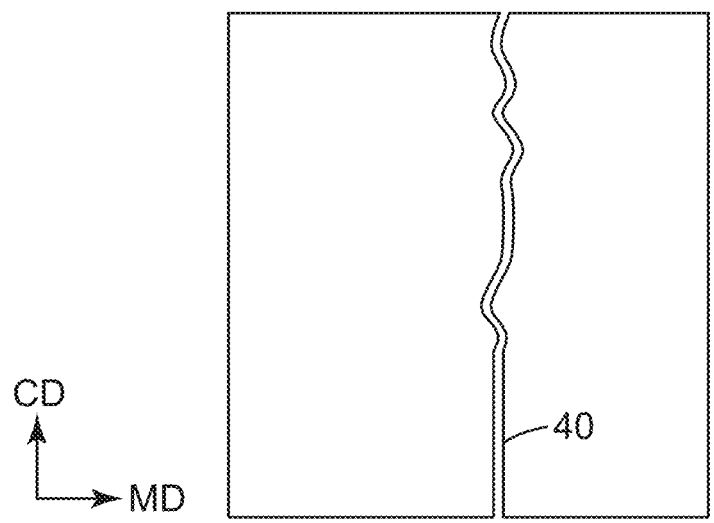
FIG. 4a is schematic illustration of a top view of Example 4 after it was evaluated for cross-direction tear propagation.
Figure 4B:
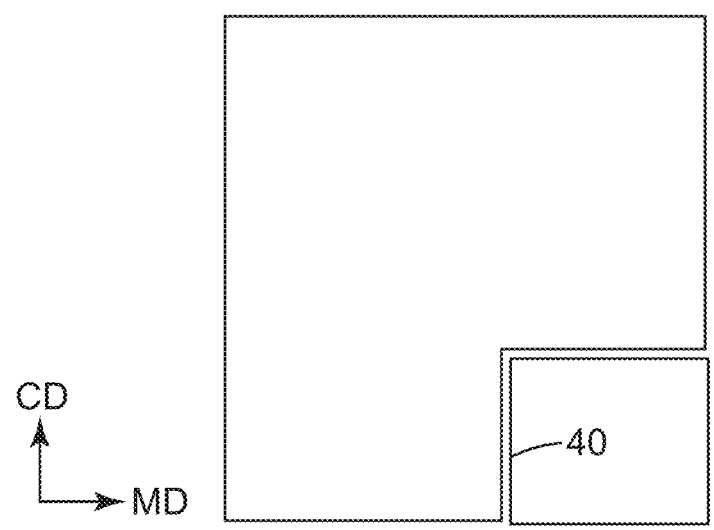
FIG. 4b is a schematic illustration of a top view of Comparative Example 4 after it was evaluated for cross-direction tear propagation.

There are differences in mechanical properties between structured films having mainly the alpha form of polypropylene and no beta nucleating agent and the structured films according to the present disclosure, as described in detail in the Examples, below. Whether stretched or not, structured films according to the present disclosure have lower tensile strength and lower stiffness than corresponding structured films having mainly the alpha form of polypropylene and no beta nucleating agent. For stretched structured films, the cross-direction tear strength of the films according to the present disclosure is higher than that of stretched structured films having mainly the alpha form of polypropylene and no beta nucleating agent. A difference in the tearing properties of the structured films having mainly the alpha form of polypropylene and no beta nucleating agent and the structured films according to the present disclosure is illustrated in FIGS. 4a and 4b. In FIG. 4a, which is a schematic illustration of a stretched structured film according to the present disclosure, notch 40 made in the cross-direction of the film will continue in the cross-direction as a tear is propagated. In contrast, in FIG. 4b, which is a schematic illustration of a stretched structured film having mainly the alpha form of polypropylene and no beta nucleating agent, notch 40 made in the cross-direction of the film will change direction resulting in a tear in the machine direction as the tear is propagated. The tear behavior of the stretched structured film according to the present disclosure provides significant manufacturing advantages over the comparative structured film. Any tear that may start in the manufacture of a continuous stretched structured film according to the present disclosure will not quickly propagate in the machine direction as would a tear in the comparative structured film.

Structured films according to the present disclosure that include both polyolefin (e.g., polypropylene) including a beta-nucleating agent and a polyolefin (e.g., polypropylene) including an alpha-nucleating, for example, in a side-by-side coextruded film can have a unique appearance. In some embodiments, first lanes comprise the semi-crystalline polyolefin and the beta-nucleating agent, and the second lanes comprise a semi-crystalline polyolefin and an alpha-nucleating agent. The side-by-side lanes may have different colors after stretching because of the micropores formed in the first lanes that are absent in the second lanes. Also, after stretching, the height of the backing in the first lanes may be larger than the height of the backing in the second lanes. If upstanding posts are capped after stretching in these applications, it may be possible to preferentially cap posts in the first lanes and not in the second lanes.

For any of the embodiments of the structured film according to and/or made according to the present disclosure, the backing may be in the form of a roll, from which smaller patches (for example, mechanical fastener patches) may be cut in a size appropriate to the desired application. In this application, the structured film may also be a patch that has been cut to a desired size, and the method of making a structured film can include cutting the film to a desired size. In some embodiments, the second surface of the backing (i.e., the surface opposite the first surface from which the upstanding posts project) may be coated with an adhesive (e.g., a pressure sensitive adhesive). In such embodiments, when the backing is in the form of a roll, a release liner may be applied to the exposed adhesive.

In some embodiments of the method of making a structured film disclosed herein, the method further comprises joining a second surface of the backing (i.e., the surface opposite the first surface from which the upstanding posts project) to a carrier. The backing may be joined to a carrier, for example, by lamination (e.g., extrusion lamination), adhesives (e.g., pressure sensitive adhesives), or other bonding methods (e.g., ultrasonic bonding, compression bonding, or surface bonding). Such joining methods may be carried out before stretching the backing or after stretching the backing, as desired. The backing may be joined to a carrier during the formation of the backing with upstanding posts. The resulting article may be a fastening laminate, for example, a fastening tab joined to the backsheet of an absorbent article useful for joining the front waist region and the rear waist region of an absorbent article.

The carrier, which in some embodiments may be joined to the second surface of the backing, may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). The term "nonwoven" when referring to a carrier or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

One or more zones of the carrier may comprise one or more elastically extensible materials extending in at least one direction when a force is applied and returning to approximately their original dimension after the force is removed. The term "elastic" refers to any material that exhibits recovery from stretching or deformation. Likewise, "nonelastic" materials, which do not exhibit recovery from stretching or deformation, may be useful for the carrier as well. In embodiments wherein the carrier is elastic and the method of making a structured film includes stretching, the joining of the carrier to the second surface of the backing is typically carried out after after stretching.

The fastening laminate that can be formed after joining the structured film disclosed herein to a carrier may be useful, for example, in absorbent articles. Exemplary absorbent articles have at least a front waist region, a rear waist region, and a longitudinal center line bisecting the front waist region and the rear waist region, wherein at least one of the front waist region or the rear waist region comprises the structured film according to and/or made according to the present disclosure. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article. The fastening laminate may also be useful, for example, for disposable articles such as sanitary napkins. A sanitary napkin typically includes a back sheet that is intended to be placed adjacent to the wearer's undergarment. The back sheet may be a structured film according to and/or made according to the present disclosure to securely attach the sanitary napkin to the undergarment, which mechanically engages with the capped posts.

In some embodiments where the carrier is a fibrous web, joining the second surface of the thermoplastic backing to a carrier comprises impinging heated gaseous fluid (e.g., ambient air, dehumidified air, nitrogen, an inert gas, or other gas mixture) onto a first surface of the fibrous web while it is moving; impinging heated fluid onto the second surface of the backing while the continuous web is moving, wherein the second surface is opposite the first surface of the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

Methods and apparatus for joining a continuous web to a fibrous carrier web using heated gaseous fluid may be found in U.S. Pat. Appl. Pub. Nos. 2011-0151171 (Biegler et al.) and 2011-0147475 (Biegler et al.), both of which are incorporated herein by reference in their entirety.

Selected Embodiments of the Disclosure

In a first embodiment, the present disclosure provides a structured film comprising a semi-crystalline polyolefin and a beta-nucleating agent, the structured film comprising a backing and upstanding posts attached to the backing.

In a second embodiment, the present disclosure provides the structured film of the first embodiment, wherein the structured film comprises beta-spherulites.

In a third embodiment, the present disclosure provides a structured film of a semi-crystalline polyolefin comprising a backing and upstanding posts attached to the backing, wherein at least the upstanding posts comprise beta-spherulites of the semi-crystalline polyolefin.

In a fourth embodiment, the present disclosure provides the structured film of any one of the first to third embodiments, wherein the backing is microporous.

In a fifth embodiment, the present disclosure provides the structured film of the fourth embodiment, wherein a density of the upstanding posts is in a range from 2 per square centimeter to 1182 per square centimeter.

In a sixth embodiment, the present disclosure provides the structured film of the fourth or fifth embodiment, wherein the structured film has a percent transmittance up to 65 percent in a wavelength range of 250 nanometers to 2250 nanometers.

In a seventh embodiment, the present disclosure provides the structured film of any one of the first to sixth embodiments, wherein the semi-crystalline polyolefin is essentially free of an infrared radiation blocking agent.

In an eighth embodiment, the present disclosure provides the structured film of any one of the first to seventh embodiments, wherein the upstanding posts have lower porosity and/or lower opacity than the backing.

In a ninth embodiment, the present disclosure provides the structured film of any one of the first to eighth embodiments, wherein the semi-crystalline polyolefin comprises polypropylene.

In a tenth embodiment, the present disclosure provides the structured film of the ninth embodiment, wherein the semi-crystalline polyolefin comprises at least one of propylene homopolymer, a copolymer of propylene and other olefins, or a blend of a polypropylene homopolymer and a different polyolefin.

In an eleventh embodiment, the present disclosure provides the structured surface of any one of the first to tenth embodiments, wherein the beta-nucleating agent is present in the structured film in a range of 1 part per million to 10,000 parts per million, based on the weight of the structured film.

In a twelfth embodiment, the present disclosure provides the structured film of any one of the first to eleventh embodiments, wherein the beta-nucleating agent is selected from the group consisting of gamma quinacridone; aluminum salt of quinizarin sulphonic acid; dihydroquinoacridin-dione; quinacridin-tetrone; triphenenol ditriazine; the combination of calcium carbonate and organic acids; the combination of calcium stearate and pimelic acid; calcium silicate; dicarboxylic acid salts of metals of Group IIA of the periodic table; delta-quinacridone; diamides of adipic or suberic acids; calcium salts of suberic or pimelic acid; indigosol or cibantine organic pigments; quinacridone quinone; N',N'-dicyclohexyl-2,6-naphthalene dicarboxamide; antraquinone red pigments; and bis-azo yellow pigments.

In a thirteenth embodiment, the present disclosure provides the structured film of any one of the first to the third embodiments, wherein a density of the upstanding posts is in a range from 10 per square centimeter to 1575 per square centimeter.

In a fourteenth embodiment, the present disclosure provides the structured film of any one of the first to thirteenth embodiments, further comprising a colorant.

In a fifteenth embodiment, the present disclosure provides the structured film of any one of the first to fourteenth embodiments, wherein the structured film is a mechanical fastener.

In a sixteenth embodiment, the present disclosure provides the structured film of the fifteenth embodiment, wherein the upstanding posts have caps distal from the backing, wherein the caps have loop-engaging overhangs.

In a seventeenth embodiment, the present disclosure provides the structured film of any one of the first to sixteenth embodiments, wherein the structured film is a multi-layer film.

In an eighteenth embodiment, the present disclosure provides the structured film of any one of the first to sixteenth embodiments, wherein the structured film is a coextruded film having side-by-side first and second lanes, wherein the first lanes comprise the semi-crystalline polyolefin and the beta-nucleating agent, and wherein the second lanes comprise a different polymer composition.

In a nineteenth embodiment, the present disclosure provides the structured film of the eighteenth embodiment, wherein the second lanes comprise an alpha-nucleating agent.

In a twentieth embodiment, the present disclosure provides the structured film of the eighteenth embodiment, wherein the second lanes comprise an elastomeric material.

In a twenty-first embodiment, the present disclosure provides the structured film of any one of the first to twentieth embodiments, wherein the structured film has a grayscale value measured in transmittance mode of up to 40.

In a twenty-second embodiment, the present disclosure provides the structured film of any one of the first to twenty-first embodiments, wherein the structured film has regions of positive and negative birefringence.

In a twenty-third embodiment, the present disclosure provides a method of making a structured film, the method comprising:
  extruding a melt of a polyolefin and a beta-nucleating agent to provide a film backing;
  cooling at least a portion of the melt to a temperature sufficient to form beta-spherulites; and
  forming upstanding posts on the film backing to provide the structured film.

In a twenty-fourth embodiment, the present disclosure provides the method of the twenty-third embodiment, wherein extruding is carried out in the presence of a tool to provide the structured film having upstanding posts on a backing.

In a twenty-fifth embodiment, the present disclosure provides the method of the twenty-third embodiment, wherein forming the upstanding posts on the film backing is carried out after cooling at least a portion of the melt.

In a twenty-sixth embodiment, the present disclosure provides the method of the twenty-third embodiment, the method further comprises stretching the film backing, and forming the upstanding posts on the film backing is carried out after stretching the film backing.

In a twenty-seventh embodiment, the present disclosure provides a method of making a structured film, the method comprising:

extruding a melt of a polyolefin and a beta-nucleating agent in the presence of a tool to provide the structured film having upstanding posts on a backing; and cooling at least a portion of the structured film to a temperature sufficient to form beta-spherulites.

In a twenty-eighth embodiment, the present disclosure provides the method of the twenty-seventh embodiment, further comprising stretching the structured film containing beta-spherulites to provide porosity in the backing.

In a twenty-ninth embodiment, the present disclosure provides the method of the twenty-sixth or twenty-eighth embodiment, wherein the stretching is carried out at a temperature in a range from 50° C. to 90° C.

In a thirtieth embodiment, the present disclosure provides the method of the twenty-sixth, twenty-eighth, or twenty-ninth embodiments, wherein the stretching is monoaxial.

In a thirty-first embodiment, the present disclosure provides the method of any one of the twenty-sixth or twenty-eighth to thirtieth embodiments, wherein stretching is carried out to provide a total stretch ratio of up to 3:1.

In a thirty-second embodiment, the present disclosure provides the method of the any one of the twenty-sixth or twenty-eighth to thirty-first embodiments, wherein the stretching is in the machine direction.

In a thirty-third embodiment, the present disclosure provides the method of the any one of the twenty-sixth or twenty-eighth to thirty-second embodiments, wherein the stretching provides an increase in opacity of at least 15 percent.

In a thirty-fourth embodiment, the present disclosure provides the method of the any one of the twenty-sixth or twenty-eighth to thirty-third embodiments, wherein the stretching provides a decrease in grayscale value measurement in transmission mode of at least 25 percent.

In a thirty-fifth embodiment, the present disclosure provides the method of any one of the twenty-third to thirty-fourth embodiments, wherein the temperature sufficient to form beta-spherulites is in a range from 90° C. to 120° C.

In a thirty-sixth embodiment, the present disclosure provides an absorbent article including the structured film of any one of the first to twenty-second embodiments or made according to any one of the twenty-third to thirty-fifth embodiments.

In a thirty-seventh embodiment, the present disclosure provides the absorbent article of the thirty-sixth embodiment, wherein the absorbent articles has at least a front waist region, a rear waist region, and a longitudinal center line bisecting the front waist region and the rear waist region, and wherein at least one of the front waist region or the rear waist region comprises the structured film.

EXAMPLES

Materials

Film grade polypropylene (PP) copolymer, a polypropylene impact copolymer, was obtained from the Dow Chemical Company, Midland, Mich., under the trade designation "DOW C700-35N POLYPROPYLENE RESIN". The polymer density was reported to be 0.902 g/cc as measured according to ASTM D972 and the melt flow index (MFI) was reported to be 35 (at 230° C. and under the load of 2.16 kg) as measured according to ASTM D1238. The beta nucleating master batch was obtained from the Mayzo Corporation, Alpharetta, Ga., under the trade designation "MPM 1114". The beta nucleating master batch was pelletized and contained a high performance beta nucleant formulation dispersed in a polypropylene homopolymer resin.

Sample Preparation

Structured films were prepared having a substantially continuous backing of thermoplastic resin and integral with the backing was an array of upstanding posts. The upstanding posts in Examples 1-4 and Comparative Examples 1-4 were capped. The cap shapes for Examples 1-4 and Comparative Examples 1-4 were oval and deformed using the procedure described in U.S. Pat. No. 6,132,660 (Kampfer) to provide "hook heads with downwardly projecting fiber engaging portions".

Example 1

The structured film with capped posts was prepared by feeding a stream of C700-35N Polyproplyene Resin (98 weight %) and the beta nucleating master batch (2 weight %) through a 2 inch single screw extruder. Barrel zones 1-7 were set at 176° C., 170° C., 180° C., 190° C., 200° C., 218° C., and 218° C., respectively. The molten resin was then fed through a sheet die to a rotating cylindrical mold. The temperature of the die was set at 218° C. and the temperature of cylindrical mold was set at 90° C. The screw speed was set at 80 rpm. Rapid flow of the resin into the mold cavities induced molecular orientation parallel to the direction of flow. The mold was water-cooled to provide rapid quenching that maintained the orientation in the polymer. The post density was 5200 posts per square inch (806 posts per square centimeter) arranged in a staggered array and the post shape was conical. The web was fed directly into a cap forming apparatus. The posts were capped with oval shaped caps using the procedure described in U.S. Pat. No. 5,845,375 (Miller et al.). The caps were subsequently deformed using the procedure described in U.S. Pat. No. 6,132,660 (Kampfer).

Example 2

The structured film with capped posts was prepared using the same processing conditions as in Example 1. In addition, the structured film from Example 1 was stretched in the machine direction using a draw ratio of 2:1 by passing the sample through a pair of rolls arranged with one roll on top of the other roll. The roll temperatures were set at 130° C.

Example 3

The structured film with capped posts was prepared using the same processing conditions described in Example 2 with the exception that during the draw the roll temperatures were set at 70° C. instead of 130° C.

Example 4

The structured film with capped posts was prepared using the same processing conditions described in Example 2 with the exception that during the draw the roll temperatures were set at 60° C. instead of 130° C.

Comparative Example 1

The structured film with capped posts was prepared according to Example 1 with the exception that the beta nucleating master batch was eliminated from the feed stream.

Comparative Example 2

The structured film with capped posts was prepared using the same processing conditions as in Comparative Example 1. In addition, the structured film from Comparative Example 1 was stretched in the machine direction using a draw ratio of 2:1 by passing the sample through a pair of rolls arranged with one roll on top of the other roll. The roll temperatures were set at 130° C.

Comparative Example 3

The structured film with capped posts was prepared using the same processing conditions described in Comparative Example 2 with the exception that during the draw the roll temperatures were set at 70° C. instead of 130° C.

Comparative Example 4

The structured film with capped posts was prepared using the same processing conditions described in Comparative Example 2 with the exception that during the draw the roll temperatures were set at 60° C. instead of 130° C.

In Table 1, the total thickness, film backing thickness, basis weight, width of web, cap diameter in the cross direction (CD), and cap diameter in the machine direction (MD) are recorded for Examples 1-4 and Comparative Examples 1-4.

TABLE 1

| Example Number | Total Thickness (μm) | Film Backing Thickness (μm) | Basis Weight (gsm) | Width of web (cm) | Cap Diameter in CD (μm) | Cap Diameter in MD (μm) |
|---|---|---|---|---|---|---|
| Example 1 | 315 | 97.0 | 112 | 20.0 | 328 | 264 |
| Example 2 | 281 | 63.0 | 60.7 | 16.6 | 330 | 258 |
| Example 3 | 285 | 67.0 | 55.3 | 17.3 | 325 | 255 |
| Example 4 | 282 | 64.0 | 53.9 | 17.9 | 335 | 250 |
| Comparative Example 1 | 327 | 97.5 | 114.5 | 14.0 | 325 | 211 |
| Comparative Example 2 | 287 | 57.2 | 71.8 | 11.5 | 308 | 223 |
| Comparative Example 3 | 285 | 55.0 | 72.1 | 11.6 | 320 | 223 |
| Comparative Example 4 | 286 | 56.3 | 72.5 | 11.8 | 315 | 210 |

The values for percent reduction in the width of web ("percent necking") after stretching and the percent reduction in the film backing thickness after stretching were calculated for Examples 2-4 and Comparative Examples 2-4 (Table 2). The percent reduction in the width of web after stretching was less for Examples 2-4, than for the corresponding Comparative Examples 2-4. Likewise, the percent reduction in the film backing thickness after stretching was less for Examples 2-4, than for the corresponding Comparative Examples 2-4.

TABLE 2

| | | | Percent Reduction After Stretching | |
|---|---|---|---|---|
| | Beta-Nucleating Agent | Roll Temperature (° C.) | for Film Backing Thickness | for Width of Web |
| Example 2 | yes | 130 | 35% | 17% |
| Example 3 | yes | 70 | 31% | 13.5% |
| Example 4 | yes | 60 | 34% | 10.5% |
| Comparative Example 2 | no | 130 | 41% | 18% |
| Comparative Example 3 | no | 70 | 44% | 17% |
| Comparative Example 4 | no | 60 | 42% | 16% |

X-Ray Diffraction

The relative levels of beta-crystals and alpha-crystals in Examples 1-4 and Comparative Examples 1-4 were determined using X-ray diffraction (Table 3). A portion of each structured film was applied to an aluminum open-backed specimen holder using double-coated tape on the edges. Reflection geometry data were collected in the form of a survey scan by use of a Philips vertical diffractometer (PANalytical, Natick, Mass.), copper Kα radiation, and proportional detector registry of the scattered radiation. The diffractometer was fitted with variable incident beam slits, fixed diffracted beam slits, and graphite diffracted beam monochromator. The survey scan was conducted from 5 to 55 degrees (2θ) using a 0.04 degree step size and 6 second dwell time. X-ray generator settings of 45 kV and 35 mA were employed.

The identification of individual peak positions was accomplished by comparison to values reported in the reference by Turner Jones, J. M. Aizlewood, and D. R. Beckett (*Die Makromolekulare Chemie*, Vol 75, Issue 1 (1964) p 134).

The diffraction patterns were subjected to profile fitting to using the analysis software JADE version 9.0 (Materials Data, Inc., Livermore, Calif.) to evaluate alpha form (110), (040), and (130) maxima as well as the beta form (300) maximum. The level of beta form present was determined as a factor (K) using the following equation: $K = I(300)_\beta / [I(300)_\beta + I(110)_\alpha + I(040)_\alpha + I(130)_\alpha]$ The individual terms of the equation are define as follows: $I(300)_\beta$ is the intensity of beta form (300) maximum; $I(110)_\alpha$ is the intensity of alpha form (110) maximum; $I(040)_\alpha$ is the intensity of alpha form (040) maximum; and $I(130)_\alpha$ is the intensity of alpha form (130) maximum. The calculated K-value varies from 0, for a sample with no beta crystals, to 1.0 for a sample with all beta-crystals.

TABLE 3

| Example | K Value |
|---|---|
| Example 1 | 0.78 |
| Example 2 | 0.27 |
| Example 3 | 0.54 |
| Example 4 | 0.60 |
| Comparative Example 1 | 0 |
| Comparative Example 2 | 0 |
| Comparative Example 3 | 0 |
| Comparative Example 4 | 0 |

Thermal Analysis

Thermal analysis measurements of Examples 1-4 and Comparative Examples 1-4 were conducted at a heating rate of 10° C./min using a model Q-2000 differential scanning calorimeter (DSC) (TA instruments, New Castle, Del.) that was calibrated for temperature and enthalpy using an indium standard having a melting point of 165.5° C. The DSC scans were run under non-isothermal conditions. Approximately 10 mg of sample was used for each run. During the first thermal scan, the sample was heated at a scanning rate of 10° C./min to 200° C. and kept at this temperature isothermally for 1 minute, in order to erase the thermal history. The samples were subsequently cooled at 10° C./min to room temperature. The samples were reheated at a rate 10° C./min up to 200° C. and the second scan results were recorded and reported. The melting temperatures ($T_m$ in ° C.) and the heat of fusion data ($\Delta H_f$ in joules/gram) for both alpha and beta phases were recorded. The melting point of the beta-crystals was generally about 10° C. to 15° C. lower than that of the alpha crystals. The results for Examples 1-4 and Comparative Examples 1-4 are presented in Table 4. Examples 1-4 exhibited dual melting temperatures that were consistent with the presence of both alpha and beta crystal phases. Comparative Examples 1-4 exhibited a single melting temperature that was consistent with the presence of only an alpha crystal phase.

TABLE 4

| Example | $T_m$ (alpha) (° C.) | $T_m$ (beta) (° C.) | $\Delta H_f$(alpha) (J/g) | $\Delta H_f$(beta) (J/g) |
|---|---|---|---|---|
| Example 1 | 164.9 | 150.7 | 25.4 | 44.14 |
| Example 2 | 164.3 | 149.3 | 36.0 | 42.0 |
| Example 3 | 164.5 | 150.2 | 26.2 | 46.0 |
| Example 4 | 165.0 | 151 | 29.3 | 44.6 |
| Comparative Example 1 | 163.1 | none | 77.6 | none |
| Comparative Example 2 | 163.2 | none | 76.6 | none |
| Comparative Example 3 | 162.9 | none | 77.0 | none |
| Comparative Example 4 | 163.4 | none | 77.5 | none |

Comparative Example 5

Comparative Example 5 was made under the same processing conditions as Example 1, except that a smooth unstructured chrome roll was used to quench the film instead of using a cylindrical tool to form the posts. Comparative Example 5 was an unstructured film containing 2% beta nucleating agent which was not stretched.

Comparative Example 6

Comparative Example 6 was made under the same processing conditions as Comparative Example 5. In addition, the film sample of Comparative Example 5 was stretched in the machine direction using a draw ratio of 2:1 by passing the sample through a pair of rolls arranged with one roll on top of the other roll. The roll temperatures were set at 60° C.

Bulk Density

The bulk density measurements (grams (g)/cubic centimeter (cc)) of Examples 1 and 4 and Comparative Examples 4, 5 and 6 were determined with a model AccuPyc 1330 gas pycnometer (Micromeritics, Norcross, Ga.) using helium as the working gas. Samples were cut in the form of small ribbons from the web, rolled and then weighed using a precision balance. The samples were loaded into a 10 cc sample chamber. The pycnometer volume analysis program was then initiated and the volume of the sample was measured five times. The arithmetic average of the five volumes was reported as the volume of the sample. The density of the samples was calculated by dividing the mass of the samples by the measured average volume. The density of the samples was measured at 24.8° C. The results for Examples 1 and 4 and Comparative Examples 4, 5, and 6 are reported in Table 5.

TABLE 5

| Example | Bulk Density (g/cc) |
|---|---|
| Example 1 | 0.8181 |
| Example 4 | 0.7423 |
| Comparative Example 4 | 0.8020 |
| Comparative Example 5 | 0.8200 |
| Comparative Example 6 | 0.7998 |

Pore Size

The pore size (μm) in the backing film of Example 4 was determined by measuring bubble point according to ASTM F-316-80. The largest effective pore size that was measured was 0.16 μm. Comparative Example 4 was also subjected to the bubble point test method, but its pore size could not be determined (ND) using this method.

Mechanical Properties

Tensile strength measurements of Examples 1-4 and Comparative Examples 1-4 were conducted according to the ASTM D-3759 using an Instron Model 1122 universal testing machine (Instron Engineering Corporation, Canton, Mass.) equipped with tensile test fixtures. For determination of tensile strength in the MD, 10.2 cm MD by 2.5 cm CD test samples were prepared. For determination of tensile strength in the CD, 10.2 cm CD by 2.5 cm MD test samples were prepared. The load at yield (in MPa) for both MD and CD was recorded as the tensile strength of the samples.

Tear strength measurements of Examples 1-4 and Comparative Examples 1-4 were determined according to ASTM D-1922 using an Elmendorf (pendulum) tear tester (ProTear model, Thwing-Albert Instruments, Philadelphia, Pa.). The tear force (grams) was measured in the MD direction using 6.3 cm MD by 5.1 cm CD test samples. The tear force (grams) was measured in the CD direction using 6.3 cm CD by 5.1 cm MD test samples. The tear strength (grams/mil) was calculated for each sample by dividing the measured tear force by the thickness (caliper) of the film backing.

The stiffness measurements of Examples 1-4 and Comparative Examples 1-4 were determined according to ASTM D-6125. Stiffness was measured in Gurley stiffness units. The following equation relates Gurley stiffness units to force:

Force (mN)=(9.807×10$^{-3}$)×(Gurley units).

The tensile strength (MPa), tear strength (g/mil), and stiffness measurements (Gurley units) for Examples 1-4 and Comparative Examples 1-4 are reported in Tables 6 and 7 for both the MD and CD directions.

TABLE 6

| Example | Tensile strength MD (MPa) | Tensile strength CD (MPa) | Tear strength MD (g/mil) | Tear strength CD (g/mil) | MD Stiffness (Gurley units) | CD Stiffness (Gurley units) |
|---|---|---|---|---|---|---|
| Example 1 | 30.9 | 30.2 | 16.2 | 25.0 | 56.7 | 57.2 |
| Example 2 | 48.6 | 15.5 | 4.9 | 18.5 | 18.3 | 10.8 |

TABLE 6-continued

| Example | Tensile strength MD (MPa) | Tensile strength CD (MPa) | Tear strength MD (g/mil) | Tear strength CD (g/mil) | MD Stiffness (Gurley units) | CD Stiffness (Gurley units) |
|---|---|---|---|---|---|---|
| Example 3 | 46.8 | 14.3 | 5.2 | 19.2 | 18.3 | 10.0 |
| Example 4 | 45.3 | 13.4 | 6.3 | 15.0 | 18.0 | 10.3 |

TABLE 7

| Example | Tensile strength MD (MPa) | Tensile strength CD (MPa) | Tear strength MD (g/mil) | Tear strength CD (g/mil) | MD Stiffness (Gurley units) | CD Stiffness (Gurley units) |
|---|---|---|---|---|---|---|
| Comparative Example 1 | 44.0 | 39.0 | 17.8 | 24.0 | 80.0 | 78.9 |
| Comparative Example 2 | 54.7 | 17.4 | 6.1 | 13.5 | 20.6 | 13.6 |
| Comparative Example 3 | 55.3 | 15.6 | 5.9 | 15.0 | 21.4 | 12.7 |
| Comparative Example 4 | 56.7 | 15.2 | 5.1 | 9.0 | 20.0 | 12.5 |

Optical Microscopy

Figure 3A:
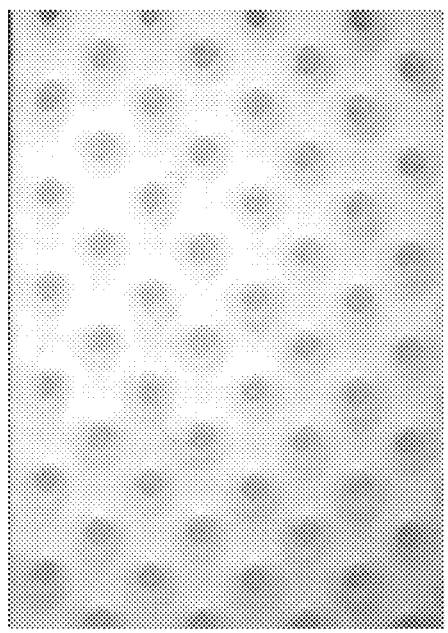
FIG. 3a is an optical microscope image of a top view of Example 4, which is an exemplary structured film according to the present disclosure where the film has been stretched.
Figure 3B:
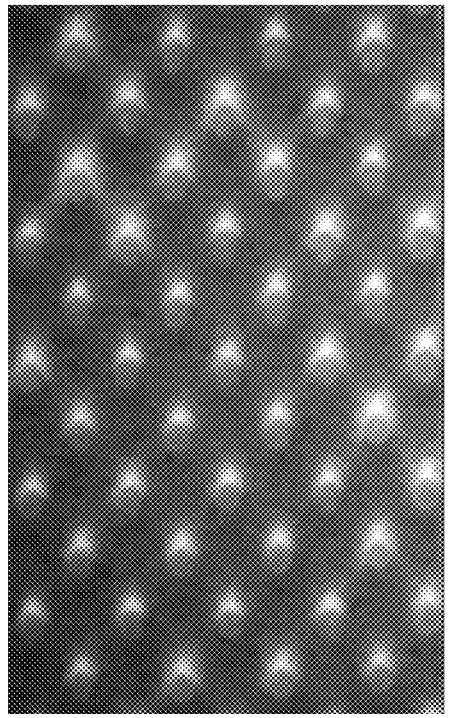
FIG. 3b is an optical microscope image of a top view of Comparative Example 4, which is a stretched structured film containing no beta-nucleating agent.

Optical microscope images were taken for Example 4 and Comparative Example 4 and are shown in FIGS. 3a and 3b, respectively. A Keyence VHS-500 model digital microscope was used, and the samples were placed against a black background when the pictures were taken.

Opacity

Opacity measurements of the structured films of Examples 1-4 were conducted according to the ASTM E-284 using a LabScan XE spectrophotometer (Hunterlab, Reston, Va.). After standardizing the sensor of the instrument, the samples are placed under the specimen port against a black back up tile and the "L" value of color measurement was recorded. The "L" value is one of three standard parameters in the CIELAB color space scale established by the International Commission on Illumination. "L" is a brightness value, ranging from 0 (black) to 100 (highest intensity). This procedure was repeated with the samples placed against a white tile. For each step the samples were rotated 90 degrees and the average of the two readings was recorded. Opacity (reported in %) was calculated by the formula: % Opacity=$(L_{Black}/L_{White})*100$. The opacity measurements are reported in Table 8.

TABLE 8

| Example | % Opacity |
|---|---|
| Example 1 | 63.3 |
| Example 2 | 74.6 |
| Example 3 | 91.4 |
| Example 4 | 92.4 |

Grayscale Measurement

Grayscale measurements of the structured films of Examples 1-4 and Comparative Examples 1-4 were collected using an IMPACT A20 digital camera (PPT Vision, Bloomington, Minn.) equipped with a CMOS (complementary metal oxide semiconductor) image sensor and the IMPACT Software Suite. The one meter long samples in the machine direction (MD) were held under tension by hand between two rollers. The samples were illuminated from behind the film side (i.e. non-post side) with a 940 nm wavelength light source. The detection camera was mounted approximately five feet above the structured film samples with the post side facing the camera. The grayscale intensity measurements were taken in the transmission mode using a numeric scale ranging from 0 (high opacity) to 255 (low opacity). The grayscale intensity was recorded at three different MD sampling points. The mean values were calculated and are reported in Table 9.

TABLE 9

| | Mean Grayscale Intensity | Sample | Mean Grayscale Intensity |
|---|---|---|---|
| Example 1 | 48 | Comparative Example 1 | 41 |
| Example 2 | 29 | Comparative Example 2 | 52 |
| Example 3 | 20 | Comparative Example 3 | 49 |
| Example 4 | 12 | Comparative Example 4 | 45 |

For comparison, a structured film with capped posts was prepared according to Comparative Example 1 with the exception that a titanium dioxide master batch (obtained from Clariant Corporation, Minneapolis, Minn.) was added to the feed stream. The titanium dioxide master batch was 50% titanium dioxide by weight and was added to the feed stream at 2% by weight, based on the total weight of the polypropylene and the master batch. The mean grayscale intensity for this film was determined to be 30 according to the test method described above. Another structured film with capped posts was prepared according to Comparative Example 1 with the exception that the titanium dioxide master batch (obtained from Clariant Corporation, added at 2% by weight as described above) was added to the feed stream, and the film was oriented in the machine direction using a draw ratio of 2:1 by passing the sample through a pair of rolls arranged with one roll on top of the other roll. The roll temperatures were set at 130° C. The mean grayscale intensity for this film was determined to be 39 according to the test method described above.

UV/Vis/NIR Spectroscopy

The transmittance and reflectance of UV/Vis/NIR (ultraviolet/visible/near infrared) radiation by Examples 1-4 and Comparative Examples 1-4 was measured using a Lambda 1050 UV/Vis/NIR spectrometer (Perkin Elmer, San Jose, Calif.) with an integrating sphere. Transmittance and reflectance spectra were recorded from 250 to 2500 nm in 5 nm increments. The integrating sphere had a diameter of 15 cm. Samples were held at 90 degrees to the incident radiation for the transmission mode and at 8 degrees in the reflectance mode. An air reference was used. For the transmission measurements, the samples are mounted with the non-post side facing the incident radiation. The percent reflectance data was collected without using the white plate (i.e. light trap) and the film side (non-post side) of the sample was mounted to face the incident beam. For analysis, the spectra were divided into three regions [250-380 nm (ultraviolet region), 380-760 nm (visible region) and 760-2250 nm (near infrared region)]. The range of values recorded for percent transmittance and percent reflectance in each region are reported in Tables 10-11.

TABLE 10

| | % Transmittance Range | | |
|---|---|---|---|
| | 250-380 nm | 380-760 nm | 760-2250 nm |
| Example 1 | 40-66 | 67-74 | 35-82 |
| Example 2 | 30-48 | 48-53 | 26-60 |
| Example 3 | 12-26 | 26-33 | 12-44 |
| Example 4 | 8-19 | 19-26 | 11-37 |
| Comp. Ex. 1 | 48-70 | 69-75 | 41-80 |
| Comp. Ex. 2 | 62-76 | 76-80 | 50-85 |
| Comp. Ex. 3 | 44-62 | 63-67 | 44-76 |
| Comp. Ex. 4 | 39-54 | 54-58 | 38-67 |

TABLE 11

| | % Reflectance Range | | |
|---|---|---|---|
| Example | 250-380 nm | 380-760 nm | 760-2250 nm |
| Example 1 | 17-32 | 29-32 | 3-29 |
| Example 2 | 39-50 | 47-50 | 22-59 |
| Example 3 | 62-73 | 69-73 | 29-69 |
| Example 4 | 70-79 | 76-79 | 38-77 |
| Comp. Ex. 1 | 18-31 | 26-30 | 1-26 |
| Comp. Ex. 2 | 19-26 | 22-25 | 6-22 |
| Comp. Ex. 3 | 32-45 | 41-44 | 12-41 |
| Comp. Ex. 4 | 26-39 | 35-38 | 10-36 |

Example 5

The structured film of Example 5 was prepared using the same processing conditions described in Example 1 with the exception that the capping procedure was not done.

Example 6

The structured film of Example 6 was prepared using the same processing conditions as in Example 5. In addition, the structured film was stretched in the machine direction using a draw ratio of 2:1 by passing the sample through a pair of rolls arranged with one roll on top of the other roll. The roll temperatures were set at 130° C.

Birefringence

The birefringence values for both the posts and film backings of Examples 5-6 and Comparative Examples 1-2 were determined. For each structured film, a sample containing three adjacent posts in the CD direction was cut from the film. A separate sample containing three adjacent posts in the MD direction was also cut from each film. The samples were cross-sectioned through the three posts in the vertical direction (perpendicular to the surface of the film backing) and the cross-sectioned face was imaged. A DMRXE microscope (Leica Microsystems GmbH, Wetzlar, Germany) with a 10×/0.25 objective was equipped with an LC-POLSCOPE retardance imaging system (Lot-Oriel GmBH & Company, Darmstadt, Germany); a RETIGA EXI FAST 1394 digital color camera (QIMAGING, Surrey BC, Canada); and a 546.5 nm interference filter (Cambridge Research and Instrumentation, Inc., Hopkinton, Mass.). For each of the six posts, the imaging system was set to record the average retardance of a 7336-pixel imaging area centered within the post, an azimuth map, a horizontal line scan, and a false-color retardance map. The birefringence value for each post was calculated using the recorded retardance measurement. The mean birefringence value (n=6) for the post element was determined and is presented in Table 12. Images of Examples 5 and 6 are shown in FIGS. 6a and 6b, respectively. Images of Comparative Examples 1 and 2 are shown in FIGS. 5a and 5b, respectively.

The cross-sectioned face of the film backing was also imaged using an imaging area defined by a 1775 pixel rectangular box. A total of six imaging areas were randomly selected in sections of the film backing located between the posts. For each of the imaging boxes, the imaging system was set to record the average retardance of the box area, an azimuth map, a horizontal line scan, and a false-color retardance map. The birefringence value for the area defined by each box was calculated using the recorded retardance measurement. The mean birefringence value (n=6) for the film backing was determined and is presented in Table 13.

TABLE 12

| Post Birefringence | |
|---|---|
| Example | Birefringence |
| Example 5 | 0.0042 |
| Example 6 | 0.0045 |
| Comparative Example 1 | 0.0023 |
| Comparative Example 2 | 0.0026 |

TABLE 13

| Film Backing Birefringence | |
|---|---|
| Example | Birefringence |
| Example 5 | 0.0035 |
| Example 6 | 0.0034 |
| Comparative Example 1 | 0.0021 |
| Comparative Example 2 | 0.0039 |

CD Tear Propagation

Tear propagation in the CD was tested for Example 4 and Comparative Example 4. Test samples (6.3 cm CD by 5.1 cm MD) were prepared and securely placed in the jaws of an Elmendorf (pendulum) tear tester (ProTear model, Thwing-Albert Instruments, Philadelphia, Pa.) making sure the bottom edge of the sample was evenly positioned on the bottom of the two jaws. A notch of approximately 2.0 cm was made in the CD (at the mid-point of the 5.1 cm side) using the knife blade on the instrument. The pendulum was released so that the specimen was torn apart. The two pieces of the torn sample were collected and the orientation of the propagation of the tear was recorded. For Example 4, the orientation of the tear continued in the CD (direction of the notch), while for Comparative Example 4 the propagation of the tear immediately turned and continued in the MD (approximately perpendicular to the direction of the notch). The results for Example 4 and Comparative Example 4 are illustrated in FIGS. 4a and 4b, respectively.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A structured film comprising a semi-crystalline polyolefin and a beta-nucleating agent, the structured film comprising a backing and upstanding posts attached to the backing, wherein the backing has a length dimension, a width dimension, and a thickness dimension, wherein the thickness dimension is the smallest dimension, wherein the backing has a first surface having the length dimension and the width dimension, and wherein the upstanding posts have base portions attached to the first surface of the backing and free ends distal from the backing.

2. The structured film of claim 1, wherein the backing is microporous, and wherein the upstanding posts have lower porosity than the backing.

3. The structured film of claim 1, wherein the backing has a greater opacity than the upstanding posts.

4. The structured film of claim 1, wherein the semi-crystalline polyolefin is substantially free of cavitating agents and substantially free of diluents that phase separate below a melting temperature of the semi-crystalline polyolefin.

5. The structured film of claim 1, wherein the semi-crystalline polyolefin comprises at least one of propylene homopolymer, a copolymer of propylene and other olefins, or a blend of a polypropylene homopolymer and a different polyolefin.

6. The structured film of claim 1, further comprising a colorant.

7. The structured film of claim 1, wherein the structured film is a mechanical fastener.

8. The structured film of claim 1, wherein the structured film is a coextruded film having side-by-side first and second lanes, wherein the first lanes comprise the semi-crystalline polyolefin and the beta-nucleating agent, and wherein the second lanes comprise a different polymer composition.

9. A structured film of a semi-crystalline polyolefin comprising a backing and upstanding posts attached to the backing, wherein the backing has a length dimension, a width dimension, and a thickness dimension, wherein the thickness dimension is the smallest dimension, wherein the backing has a first surface having the length dimension and the width dimension, wherein the upstanding posts have base portions attached to the first surface of the backing and free ends distal from the backing, and wherein at least the upstanding posts comprise beta-spherulites of the semi-crystalline polyolefin.

10. The structured film of claim 9, wherein the backing is microporous, and wherein the upstanding posts have lower porosity than the backing.

11. The structured film of claim 9, wherein the backing has a greater opacity than the upstanding posts.

12. The structured film of claim 9, wherein the semi-crystalline polyolefin is substantially free of cavitating agents and substantially free of diluents that phase separate below a melting temperature of the semi-crystalline polyolefin.

13. The structured film of claim 9, wherein the semi-crystalline polyolefin comprises at least one of propylene homopolymer, a copolymer of propylene and other olefins, or a blend of a polypropylene homopolymer and a different polyolefin.

14. The structured film of claim 9, further comprising a colorant.

15. A method of making the structured film of claim 1, the method comprising:
    extruding a melt of a polyolefin and a beta-nucleating agent in the presence of a tool to provide the structured film having upstanding posts on a backing; and
    cooling at least a portion of the structured film to a temperature sufficient to form beta-spherulites.

16. The method of claim 15, further comprising stretching the structured film containing beta-spherulites to provide porosity in the backing.

17. The method of claim 16, wherein the stretching is carried out at a temperature in a range from 50° C. to 90° C.

18. The method of claim 16, wherein the stretching is monoaxial.

19. The method of claim 16, wherein stretching is carried out to provide a total stretch ratio of up to 3:1.

20. The method of claim 16, wherein the stretching provides an increase in opacity of at least 15 percent.

* * * * *